United States Patent
Parsons et al.

(10) Patent No.: US 9,448,147 B2
(45) Date of Patent: *Sep. 20, 2016

(54) MULTI-DIMENSIONAL CHROMATOGRAPHIC METHODS FOR SEPARATING N-GLYCANS

(71) Applicant: MOMENTA PHARMACEUTICALS, INC., Cambridge, MA (US)

(72) Inventors: Ian Christopher Parsons, Belmont, MA (US); Ting Zheng, Lake Oswego, OR (US); Nur Sibel Gunay, Chestnut Hill, MA (US); Carlos J. Bosques, Arlington, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 288 days.

This patent is subject to a terminal disclaimer.

(21) Appl. No.: 14/074,807

(22) Filed: Nov. 8, 2013

(65) Prior Publication Data

US 2014/0065716 A1    Mar. 6, 2014

Related U.S. Application Data

(63) Continuation of application No. 13/630,594, filed on Sep. 28, 2012, now Pat. No. 8,703,498, which is a continuation of application No. 12/595,937, filed as application No. PCT/US2008/060346 on Apr. 15, 2008, now Pat. No. 8,304,250.

(60) Provisional application No. 60/923,705, filed on Apr. 16, 2007.

(51) Int. Cl.
*G01N 1/34* (2006.01)
*B01D 15/18* (2006.01)
*C07K 1/36* (2006.01)
*G01N 30/46* (2006.01)

(52) U.S. Cl.
CPC ............ *G01N 1/34* (2013.01); *B01D 15/1864* (2013.01); *C07K 1/36* (2013.01); *G01N 30/463* (2013.01); *Y10T 436/14* (2015.01); *Y10T 436/142222* (2015.01); *Y10T 436/143333* (2015.01); *Y10T 436/145555* (2015.01)

(58) Field of Classification Search
CPC .. B01D 15/1864; C07K 1/36; G01N 30/463; G01N 1/34; Y10T 436/145555; Y10T 436/14; Y10T 436/143333; Y10T 436/142222
See application file for complete search history.

(56) References Cited

U.S. PATENT DOCUMENTS 5,747,347 A    5/1998   Hawke et al.
8,304,250 B2 *   11/2012   Parsons .............. B01D 15/1864
                                                                                        436/86
8,703,498 B2 *   4/2014   Parsons .............. B01D 15/1864
                                                                                        436/86
2006/0057638 A1    3/2006   Bosques et al.
2006/0127950 A1    6/2006   Bosques et al.

FOREIGN PATENT DOCUMENTS

WO    WO-2005026720 A1    3/2005
WO    WO-2005111627 A2    11/2005
WO    WO-2007012695 A2    2/2007

OTHER PUBLICATIONS

Anumula, Advances in fluorescence derivatization methods for high-performace liquid chromatographic anaylsis of glycoprotein carbohydrates, Analytical Biochemistry, 350:1-23 (2006).
Balshusemann et al., The oligosaccharides of the glycoprotein pheromone of Volvox carteri f.nagariensis Iyengar (Chlorophyceae), Eur. J. Biochem, 192:231-237 (1990).
Bigge et al., Nonselective and efficient fluorescent lebling of glycans using 2-amino benzamide and anthranilic acid, Analytical Biochemistry, 230: 229-238 (1995).
Chen et al., Neutral N-glycans in adult rat brain tissue-complete characterization reveals fucosylated hybrid and complex structures, Eur. J. Biochem, 251: 691-703 (1998).
Chen et al., New methods for rapid separation and detection of oligosaccharides from glycoproteins, FASEB Journal, 2:2819-2824 (1988).
Cipollo et al., N-glycans of Caenorhabditis elegans are specific to developmental stages, J. Bio. Chem., 280:26063-26072 (2005).
Deguchi et al., Two dimensional hydrophilic interaction chromatography coupling anionexchange and hydrophilic interaction columns for separation of 2-pyridylamino derivatives of neutral and sialylated N-glycans, J. Chromatography A, 1189:169-174 (2008).
Fong et al., Fractionation of bovine whey proteins and characterisation by proteomic Techniques, International Dairy Journal, 18:23-46 (2007).
Gao et al., Alternative sources of reagents and supplies for fluorophore-assisted carbohydrate electrophoresis (FACE), Glycobiology, 13:1G-3G (2003).
Gennaro et al., Reversed-phase ion-pairing liquid chromatography/ion trap mass spectrometry for the analysis of negatively charged, derivatized glycans, Rapid Comm. Mass Spec., 17:1528-1534 (2003).
Grimm et al., Capillary liquid chromatographic and automated MALDI-TOF mass spectrometric analysis of complex carbohydrate mixtures, Anal. Chem., 70:3840-3844 (1998).
International Search Report for PCT/US2008/060346 mailed Jul. 10, 2008.
Itoh et al., Simultaneous microanalysis of N-linked oligosaccharides in a glycoprotein using microbore graphitized carbon column liquid chromatography-mass spectrometry J. Chromatography A, 968:89-100 (2002).

(Continued)

*Primary Examiner* — Christopher A Hixson
(74) *Attorney, Agent, or Firm* — Choate, Hall & Stewart LLP

(57) ABSTRACT

A multi-dimensional chromatographic method for the separation of N-glycans. The method comprises providing a glycan preparation that includes at least one negatively charged N-glycan. The glycan preparation is then separated by anion-exchange chromatography and at least one secondary chromatographic technique.

20 Claims, 33 Drawing Sheets

(56) References Cited

OTHER PUBLICATIONS

Joo An et al., Determination of N-Glycosylation Sites and Site Heterogeneity in Glycoproteins, Analytical Chem., 75:5628-5637 (2003).
Kamerling, Structural studies on glycoprotein glycans, Pure Appl. Chem., 66:2235-2238 (1994).
Kawar et al., N-Glycan processing by a lepidopteran insect α1,2-mannosidase, Glycobiology, 10(4):347-355 (2000).
Kawasaki et al., Microanalysis of N-linked oligosaccharides in a glycoprotein by capillary liquid chromatography/mass spectrometry and liquid chromatography/tandem mass spectrometry, Analytical Biochemistry, 316:15-22 (2003).
Kawasaki et al., Structural analysis of sulfated N-Linked oligosaccharides in erythropoietin Glycobiology, 11:1043-1049 (2001).
Kishino et al., Purification Method for alpha-1-acid glycoprotein with subsequent high-performance liquid chromatographic determination of monosaccharides in plasma of healthy subject and patients with renal insufficiency, Journal of Chromatography B: Biomedical Sciences and Applications, 672:199-205 (1995).
Kuraya et al., Analysis of pyridylaminated O-linked sugar chains by two-dimensional sugar mapping, Anal. Biochem, 233:205-211 (1996).
Lamari, et al., Derivatization of carbohydrates for chromatographic, electrophoretic and mass spectrometric structure analysis Journal of Chromatography B, 793:15-36 (2003).
Martin, Separation of N-glycans by HPLC, Methods in Molecular Biology, Humana Press Inc., 45-61 (2002).
Nakagawa et al., Identification of Neutral and Sialyl N-Linked Oligosaccharide Structures from Human Serum Glycoproteins Using Three Kinds of High-Performance Liquid Chromatography, Analytical Biochemistry, 226:130-138 (1995).
Nakagawa et al., Nomenclature Committee of the International Union of Biochemistry and Molecular Biology, Eur. J. Biochem., 237:76-85 (1996).
O'Neill, Enzymatic release of oligosaccharides from glycoproteins for chromatographic and electrophoretic analysis, Journal of Chromatography A, 720:201-215 (1996).
Pace et al., Characterization of Minor N-linked Glycans on Antibodies Using Endo H Release and MALDI-Mass Spectrometry, Analytical Letters, 42:1711-172 (2009).
Pesek et al., How to Retain Polar and Nonpolar Compounds on the Same HPLC Stationary Phase with Isocratic Mobile Phase, LCGC, 24:296-303 (2006).
Pesek et al., Synthesis and characterization of chemically bonded stationary phases on hydride surfaces by hydrosilation of alkynes and dienes, Journal of Separation Science, 28:2437-2443 (2005).
Pesek et al., Synthesis and HPLC evaluation of carboxylic acid phases on a hydride surface, Journal of Separation Science, 29:872-880 (2006).
Pfeiffer et al., Separation of glycoprotein-N-glycans by high-pH anion-exchange chromatoghraphy Biochemical Chromatography, 4:193-199 (1990).
Prime et al., Oligosaccharide sequencing based on exo- and endoglycosidase digestion and liquid chromatographic analysis of the products, Journal of Chromatography A, 720:263-274 (1996).
Royle et al., An analytical and structural database provides a strategy for sequencing O-glycans from microgram quantities of glycoproteins, Anal. Biochem,, 304:70-90 (2002).
Succari et al., Two-step purification of human $\alpha_1$-acid glycoprotein, Journal of Chromatography, 341:457-461 (1985).
Takahashi et al., N-glycan structures from the major glycoproteins of pigeon egg white, J. Biological Chemistry, 276( 26):23230-23239 (2001).
Takahashi et al., Three-dimensional elution mapping of pyridylaminated N-linked neutral and sialyl oligosaccharides, Analytical Biochemistry, 226:139-146 (1995).
Takahashi et al., N-glycan structures of a recombinant mouse soluble FCγ receptor II Glycoconjugate Journal, (1998) vol. 15:905-914.
Takahashi et al., N-glycan structures of murine hippocampus serine protease, neuropsin, produced in Trichoplusia ni cells, Glycoconjugate Journal, 16:405-414 (1999).
Takahashi et al., On peptide bond formation, translocation, nascent protein progression and the regulatory properties of ribosomes, Eur. J. Biochem., 270:2627-2632 (2003).
Takahashi et al., Two Dimensional Elution Map of GalNAc-Containing N-Linked Oligosaccharides, Analytical Biochemistry, 208:96-109 (1993).
Takegawa et al., Separation of isomeric 2-aminopyridine derivatized N-glycans and N-glycopeptides of human serum immunoglobulin G by using a zwitterionic type of hydrophilic-interaction chromatography, J. Chromatography A, 1113:177-181 (2006).
Tomiya et al., Analyses of N-linked oligosaccharides using a two-dimensional mapping technique, Analytical Biochemistry, 171:73-90 (1988).
Tomiya et al., Contribution of Component Monosaccharides to Coordinates of Neutral and Sialyl Pyridylaminated N-Glycans on a Two-Dimensional Sugar Map, Analytical Biochemistry, 264:204-210 (1998).
Written Opinion for PCT/US2008/060346 mailed Jul. 10, 2008.
Xia et al., Versatile fluorescent derivatization of glycans for glycomic analysis, Nature Methods, 2(11):845-850 (2005).
Yagi et al., Development of structural analysis of sulfated N-glycans by multidimensional high performance liquid chromatography mapping methods, Glycobiology, 15:1051-1060 (2005).
Yuen et al., High-performance liquid chromatographic profiling of fluorescent labeled N-glycans on glycoproteins, Biomedical Chromatography, 16:247-254 (2002).

* cited by examiner

NA4 N-linked oligosaccharide.

NGA4 N-linked oligosaccharide.

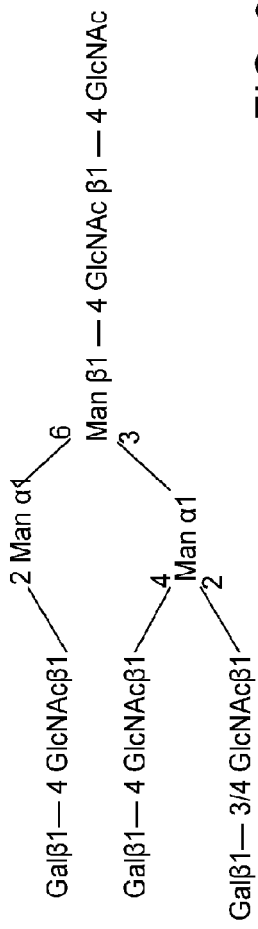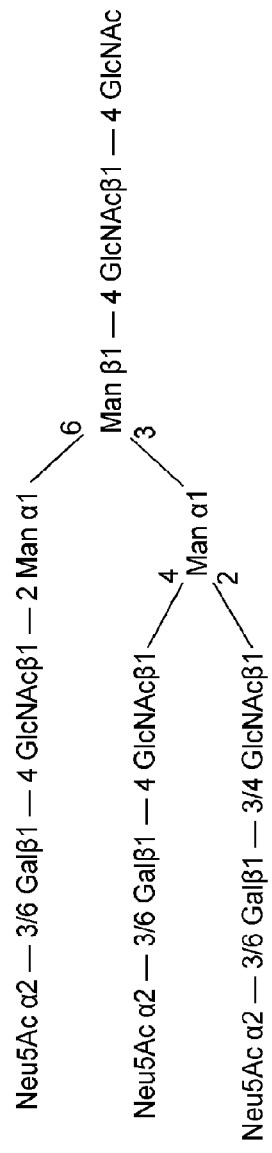

Synonyms: NA3 N-linked oligosaccharide.

Synonyms: A2F N-linked oligosaccharide.

Synonyms: NGA3 N-linked oligosaccharide.

Synonyms: A1F N-linked oligosaccharide.

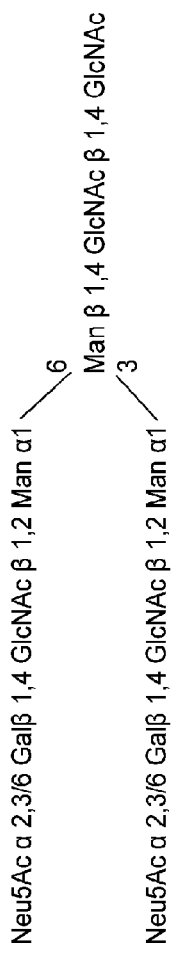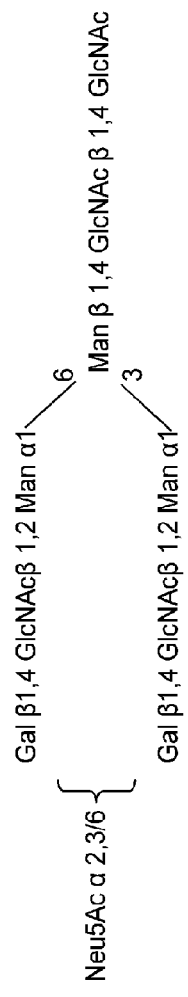

Structure

Synonyms: NA2 N-linked oligosaccharide.

Synonyms: NGA2 N-linked oligosaccharide.

Structure

Synonyms: M3N2 N-linked oligosaccharide.

Synonyms: Hybrid N-linked oligosaccharide.

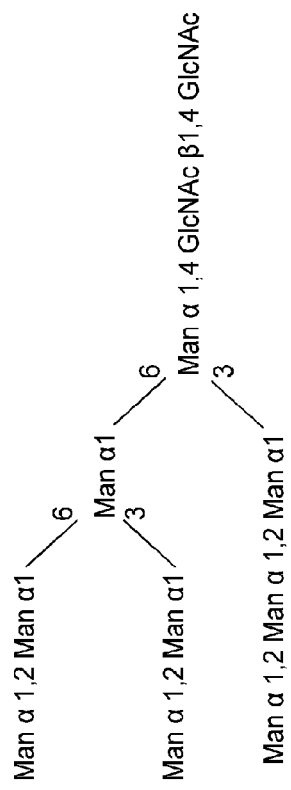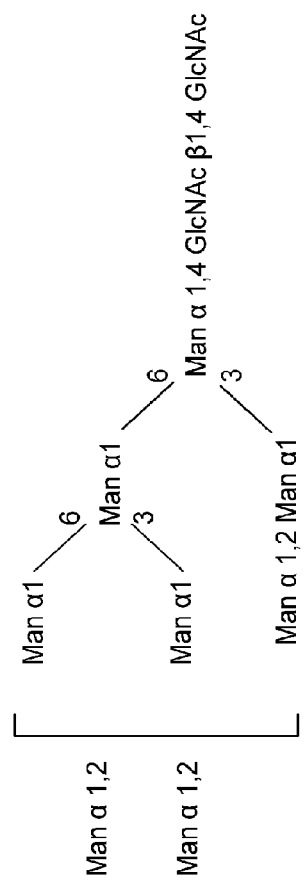
Synonyms: Man-9 N-linked oligosaccharide. Oligomannose 9 glycan.  FIG. 3Q
Synonyms: Man-8 N-linked oligosaccharide. Oligomannose 8 glycan.  FIG. 3R Synonyms: Man-7 N-linked oligosaccharide. Oligomannose 7 glycan.

Synonyms: Man-6 N-linked oligosaccharide. Oligomannose 6 glycan.

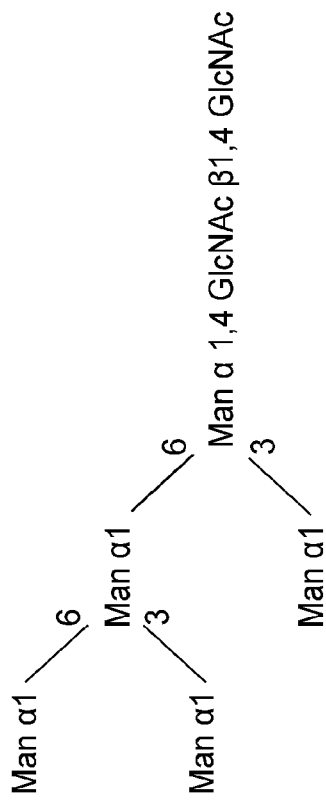

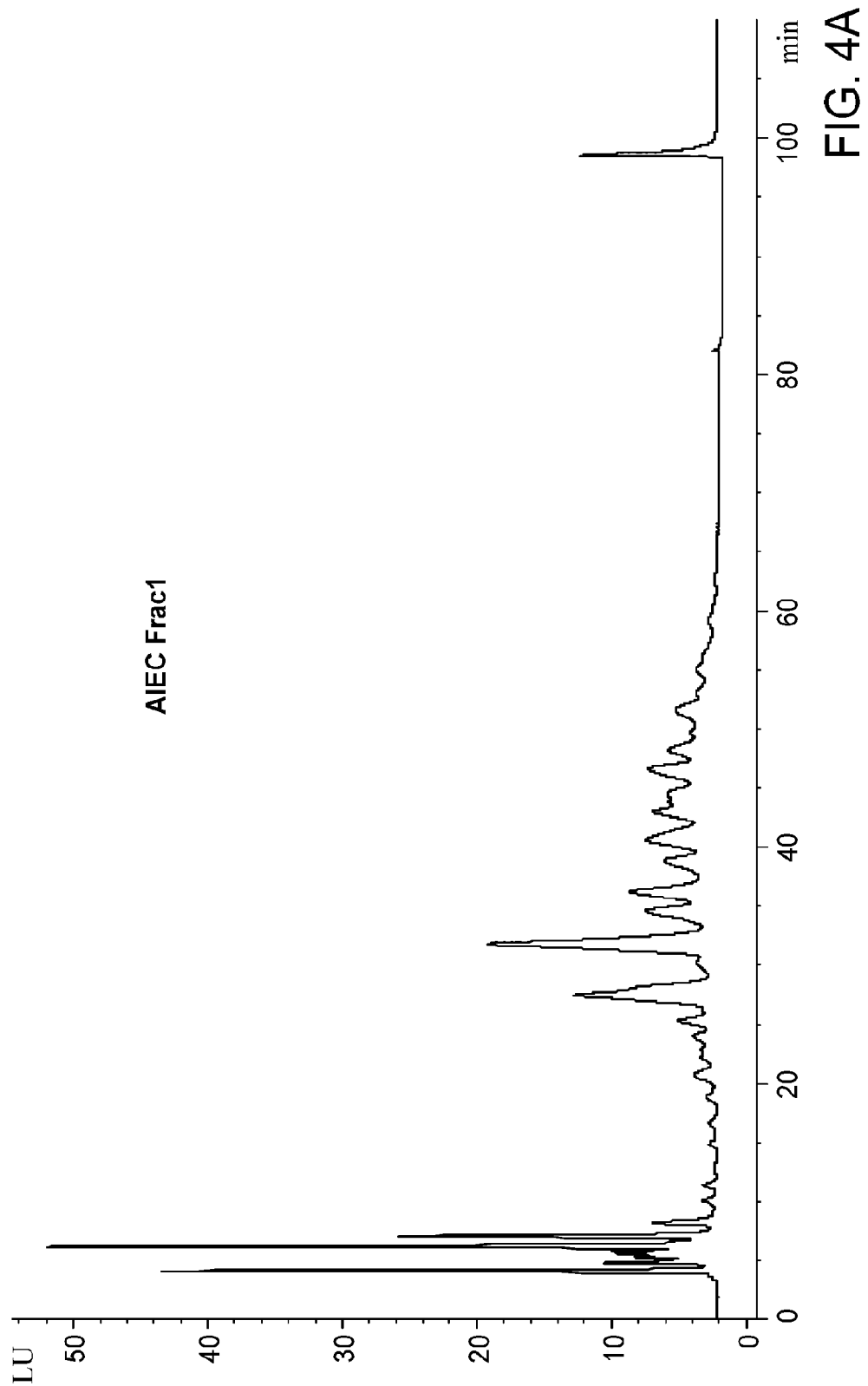

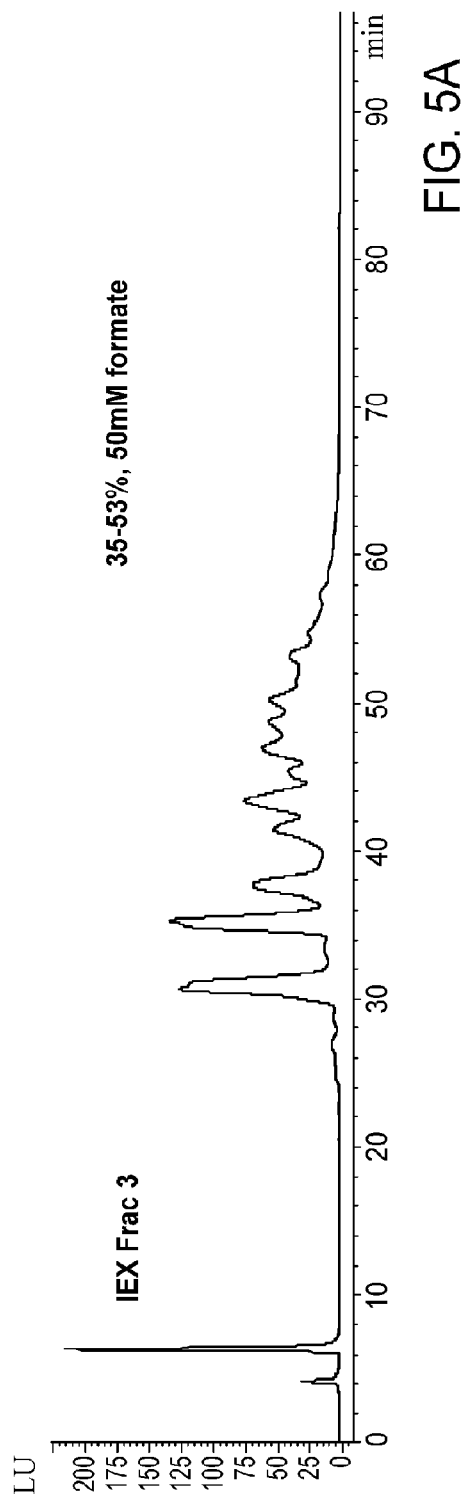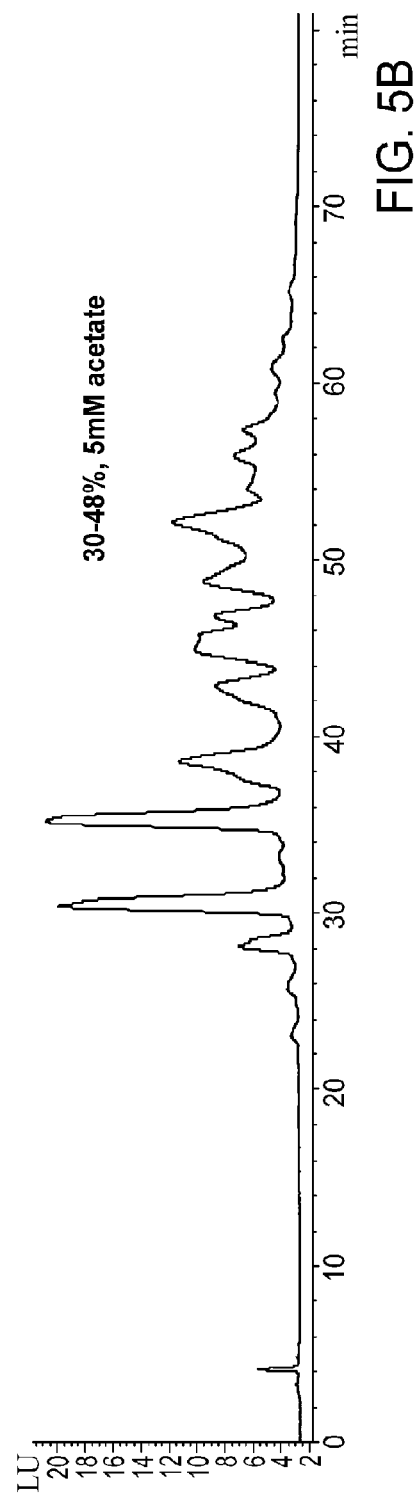
FIG. 5A
FIG. 5B

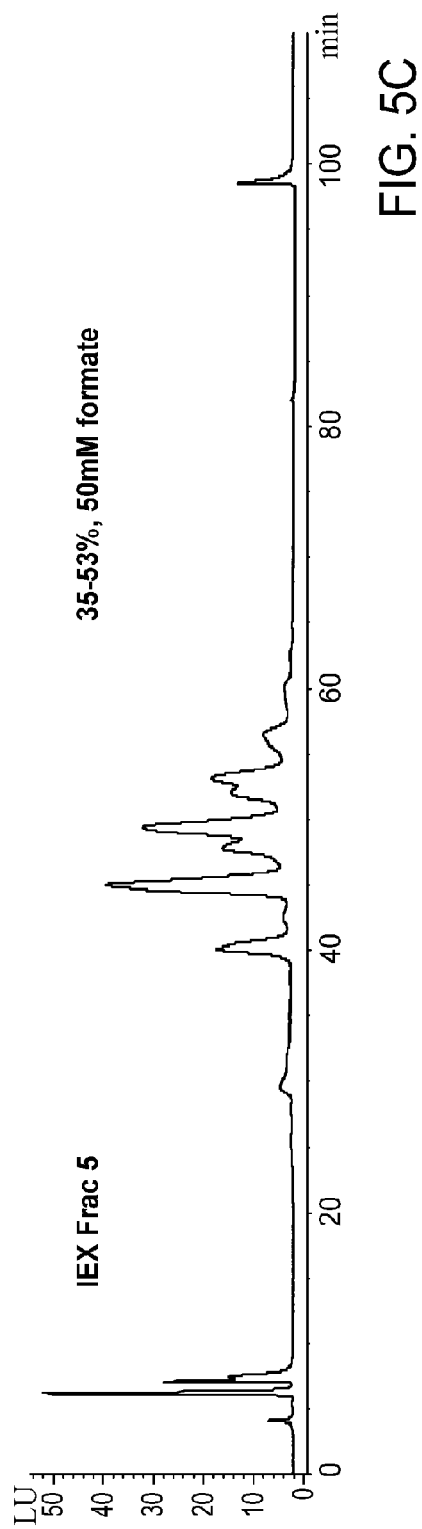
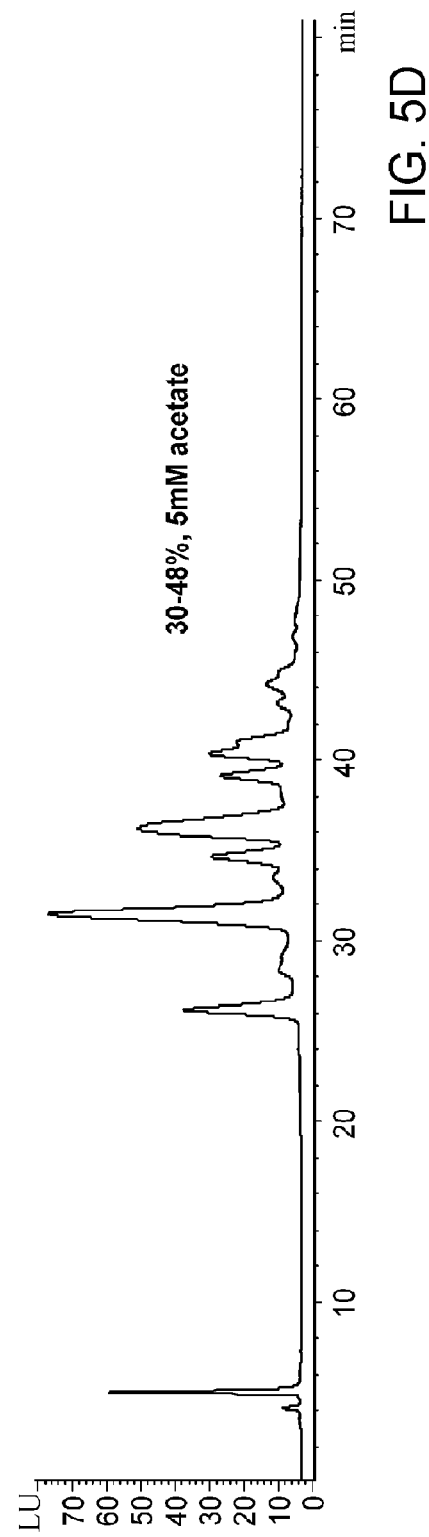
FIG. 5C
FIG. 5D

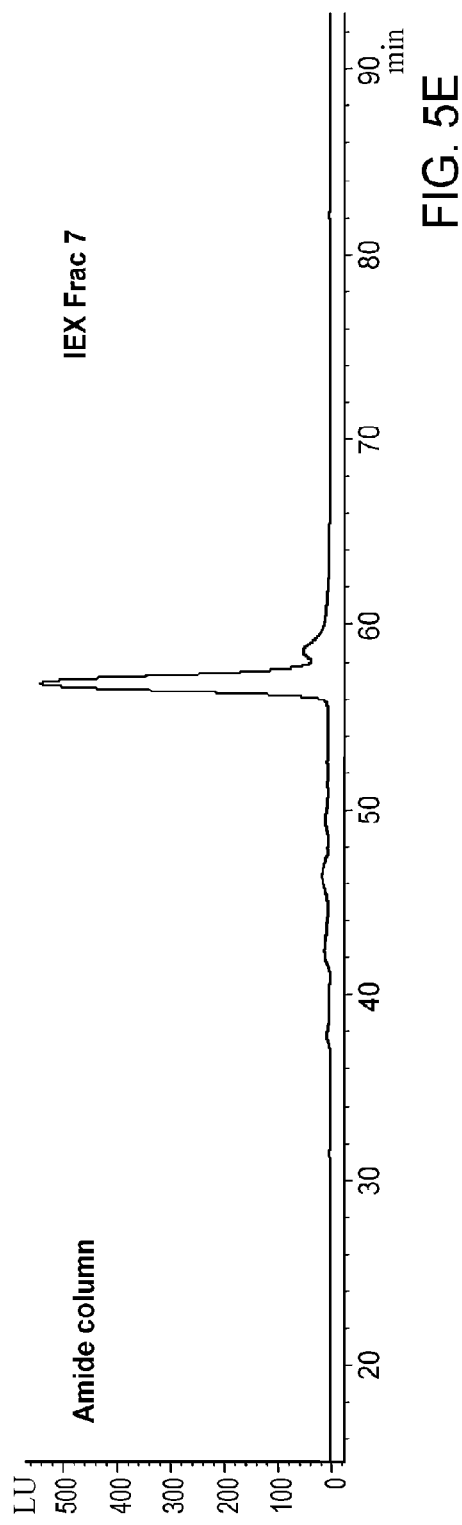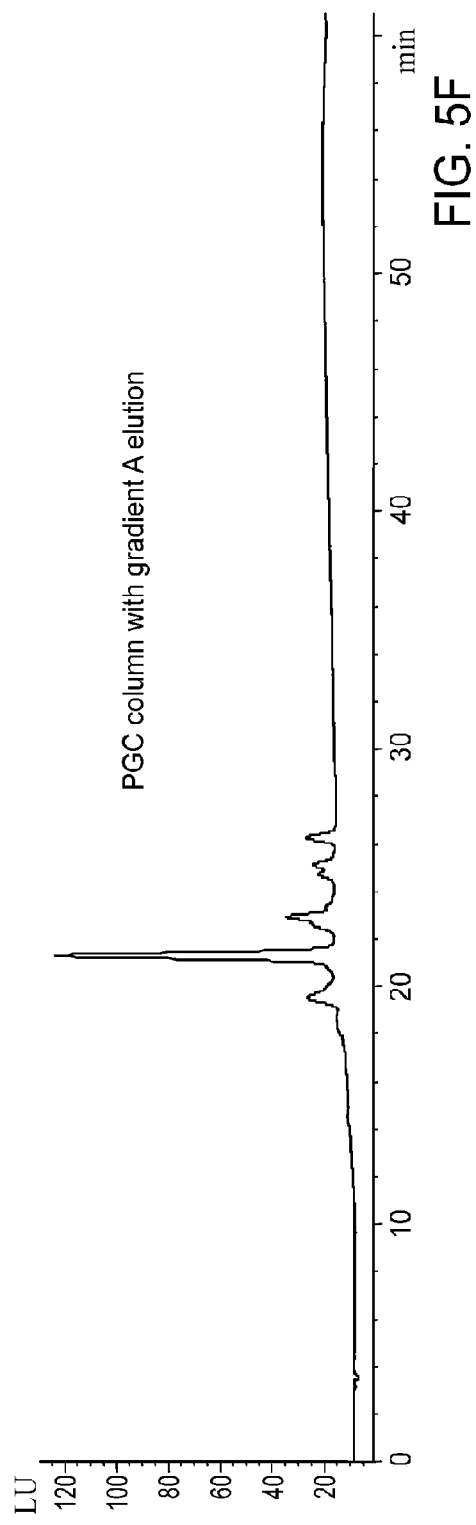
FIG. 5E
FIG. 5F

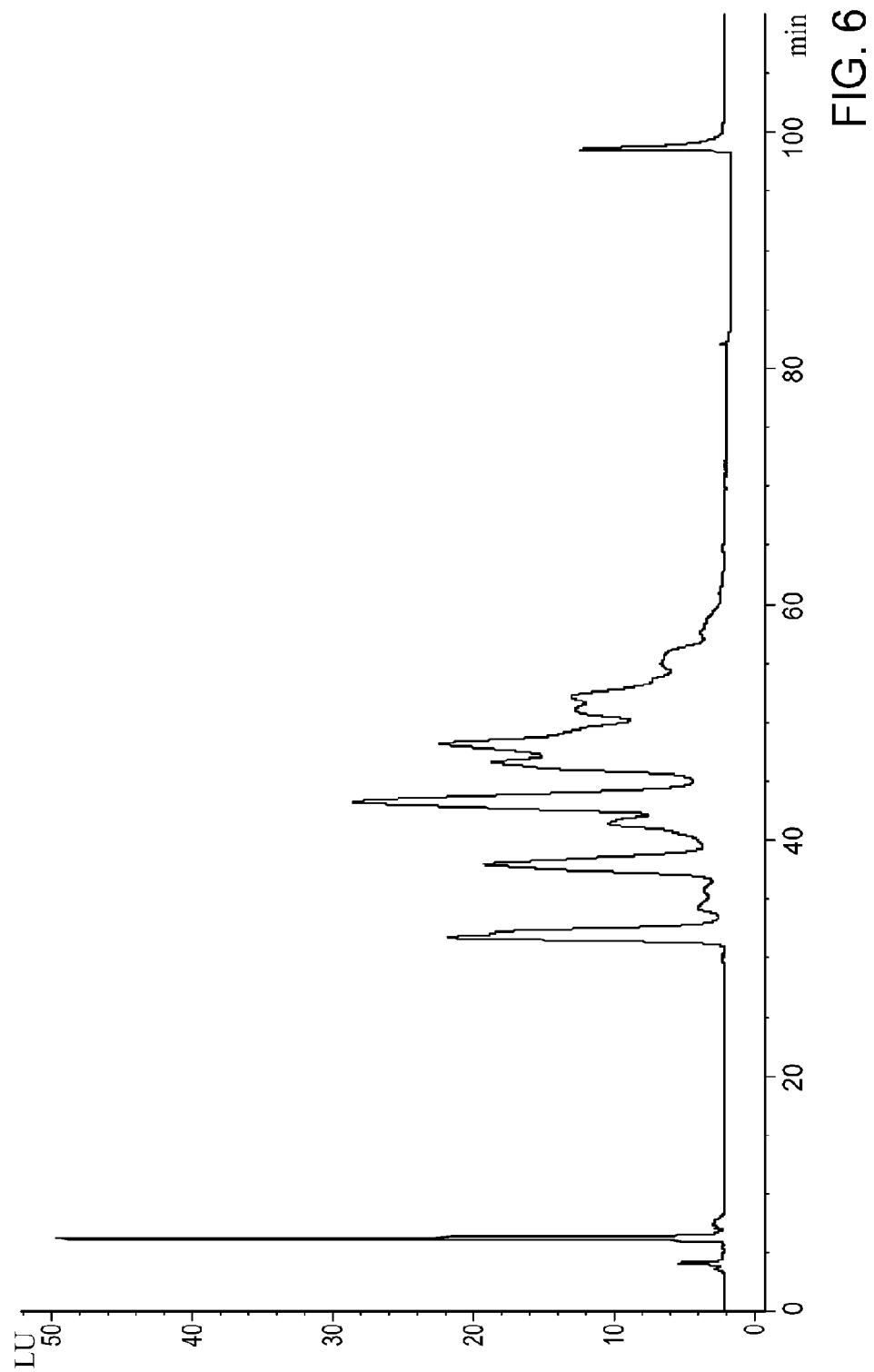

MULTI-DIMENSIONAL CHROMATOGRAPHIC METHODS FOR SEPARATING N-GLYCANS

CROSS-REFERENCE TO RELATED APPLICATIONS

This application is a continuation of U.S. application Ser. No. 13/630,594, filed Sep. 28, 2012, which is a continuation of U.S. application Ser. No. 12/595,937, filed Oct. 14, 2009, now U.S. Pat. No. 8,304,250, which claims the benefit under 35 U.S.C. 371 of International Application Number PCT/US08/60346 (published on Oct. 23, 2008, as PCT publication number WO 2008/128225), filed Apr. 15, 2008, which claims priority to U.S. Provisional Application No. 60/923,705, filed Apr. 16, 2007, the entire contents of each of which are incorporated herein by reference.

BACKGROUND

Sugar-containing biomolecules, such as glycans and glycoconjugates, provide significant challenges in their characterization, quantification, purification, and structure elucidation. Such challenges stem from an inherent conformational complexity and structural diversity, as well as other physical features, such as instability to isolation conditions, high or low pH, or elevated temperatures.

These challenges are compounded when the biomolecule is provided in a complex mixture. Such a scenario demands use of separation techniques and careful handling of the sample. Most separations involve derivatization of the glycan with a suitable label (e.g., a chromophore), separation of a desired derivatized glycan from a mixture via a separation technique, purification, and so on, followed by structure determination. In some cases, the above methods may also include release of the glycan component from a glycoconjugate by chemical or enzymatic cleavage prior to derivatization and separation. While methods for separating glycan mixtures have been described in the art there remains a need for other methods.

SUMMARY

The present disclosure provides a multi-dimensional chromatographic method for the separation of N-glycans. The method comprises providing a glycan preparation that includes at least one negatively charged N-glycan. The glycan preparation is then separated by anion-exchange chromatography and at least one secondary chromatographic technique.

Two-dimensional and three-dimensional mapping techniques of N-linked oligosaccharides have been described by Takahashi and co-workers (see, for example, Takahashi et al., *Analytical Biochemistry* (1993) 208:96-109; Nakagawa et al., *Eur. J. Biochem.* (1996) 237:76-85; Takahashi et al., *Glycoconjugate Journal* (1998) 15:905-914; Tomiya and Takahashi, *Analytical Biochemistry* (1998) 264:204-210; Takahashi et al., *Glycoconjugate Journal* (1999) 16:405-414; Takahashi et al., *Eur. J. Biochem.* (2003) 270:2627-2632; and Yagi et al., *Glycobiology* (2005) 15:1051-1060). This mapping involves chromatographic analysis of a large selection of known oligosaccharides using fixed standard parameters (e.g., the same column types, the same elution rates and same elutant etc.) in order to provide a comprehensive "map" of their elution positions. The relative structure of unknown N-linked oligosaccharides can be estimated by comparing the elution position (expressed in glucose units) of an unknown sample with those of the standard oligosaccharides.

By contrast, the present disclosure provides flexible (i.e., not fixed) procedures that can be tailored for the separation of individual N-glycans from glycan preparations. Among other things, the present disclosure demonstrates the particular utility of an anion exchange column, followed by a second separation, in order to isolate and/or analyze N-linked glycans. These techniques do not employ fixed standard parameters. Rather, the methods can be varied, for example, depending on the glycan being separated and/or on the source of the initial glycan prepartion. For example, upon separation of a particular glycan preparation in the first dimension, individual fractions are obtained which comprise one or more N-glycans. Second dimensional parameters (e.g., column type, elution rate, elutant) can then be tuned to each individual fraction in order to optimize separation of individual N-glycans from that fraction. In general, the inventors have found that, depending upon the glycan preparation, good resolution of earlier fractions (e.g., such as the first half to two-thirds of the fractions) can be obtained using a normal phase column in the second dimension, and good resolution of later fractions (e.g., such as the last half to one-third of the fractions) can be obtained using reverse phase column in the second dimension. In fact, the inventors have surprisingly found that a reverse phase porous graphatized carbon (PGC) often effects better separation of later fractions than does a normal phase amide column.

Depending upon the quality of separation in the second dimension, additional separations using additional dimensions may be employed. Thus, each dimension may employ different parameters, and within each second, third, fourth, fifth, etc. dimension, separation parameters can vary from fraction to fraction.

DEFINITIONS

Approximately, About: As used herein, the term "approximately" or "about," as applied to one or more values of interest, refers to a value that is similar to a stated reference value. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the disclosure, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfonacetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform", is used herein to refer to a particular form of a glycoconjugate. That is, when the same backbone moiety (e.g., polypeptide, lipid, etc.) that is part of a glycoconjugate has the potential to be linked to different glycans or sets of glycans, then each different version of the glycoconjugate (i.e., where the backbone is linked to a particular set of glycans) is referred to as a "glycoform".

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments of the disclosure, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments of the disclosure, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycosidase: The term "glycosidase" as used herein refers to an agent that cleaves a covalent bond between sequential sugars in a glycan or between the sugar and the backbone moiety (e.g. between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans. A glycosylation pattern can be characterized by, for example, the identities of glycans, amounts (absolute or relative) of individual glycans or glycans of particular types, degree of occupancy of glycosylation sites, etc., or combinations of such parameters.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

N-glycan: The term "N-glycan", as used herein, refers to a polymer of sugars that has been released from a glyconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exist, but are typically based on the common core pentasaccharide $(Man)_3(GlcNAc)(GlcNAc)$.

O-linked glycans: O-linked glycans are glycans that are linked to a glyconconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Resin: As used herein, a "resin" is an organic polymer. The polymer may be naturally occurring or synthetic.

Secondary chromatographic technique: As used herein, a "secondary chromatographic technique" refers to a chromatographic technique which is used to further separate at least a portion of the product from a first separation. In one embodiment, the secondary chromatographic technique is different from the one that was used to perform the first separation. The primary and secondary chromatographic techniques may differ in kind (e.g., anion-exchange chromatography vs. affinity chromatography) or degree (e.g., two anion-exchange chromatographic techniques that use different elution buffers).

Sialic acid: The term "sialic acid", as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylization, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

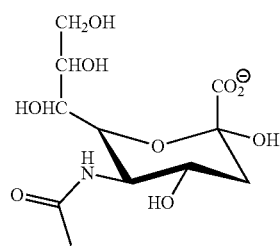

N-acetylneuraminic acid (Neu5Ac)

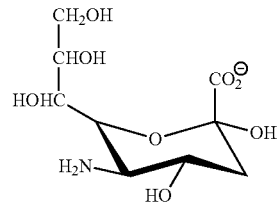

Neuraminic acid (Neu)

BRIEF DESCRIPTION OF THE DRAWING

FIGS. 4A-4J. Representative chromatograms depicting separation of N-glycan fractions obtained after anion-exchange chromatography by normal-phase amide chromatography relative to a labeled standard (left peak).

FIGS. 5A-5G. Exemplary chromatograms depicting separation of N-glycan fractions (e.g., fraction 3, 5 and 7 of a sample) obtained from anion-exchange chromatography by tuning the gradient and column type of the second dimension to the content of each particular fraction. For example, a more shallow second dimension (30-48%) gradient on a normal phase amide column effected better separation of fractions 3 and 5 than a steeper (35-53%) gradient (compare A with B and C with D). Better separation was found using the porous graphitized carbon (PGC) column versus a normal phase amide column for fraction 7 (compare E with F and G).

FIG. 6. Chromatographic resolution of glycans by a second dimensional amide column method.

DETAILED DESCRIPTION OF CERTAIN EMBODIMENTS

Figure 1:
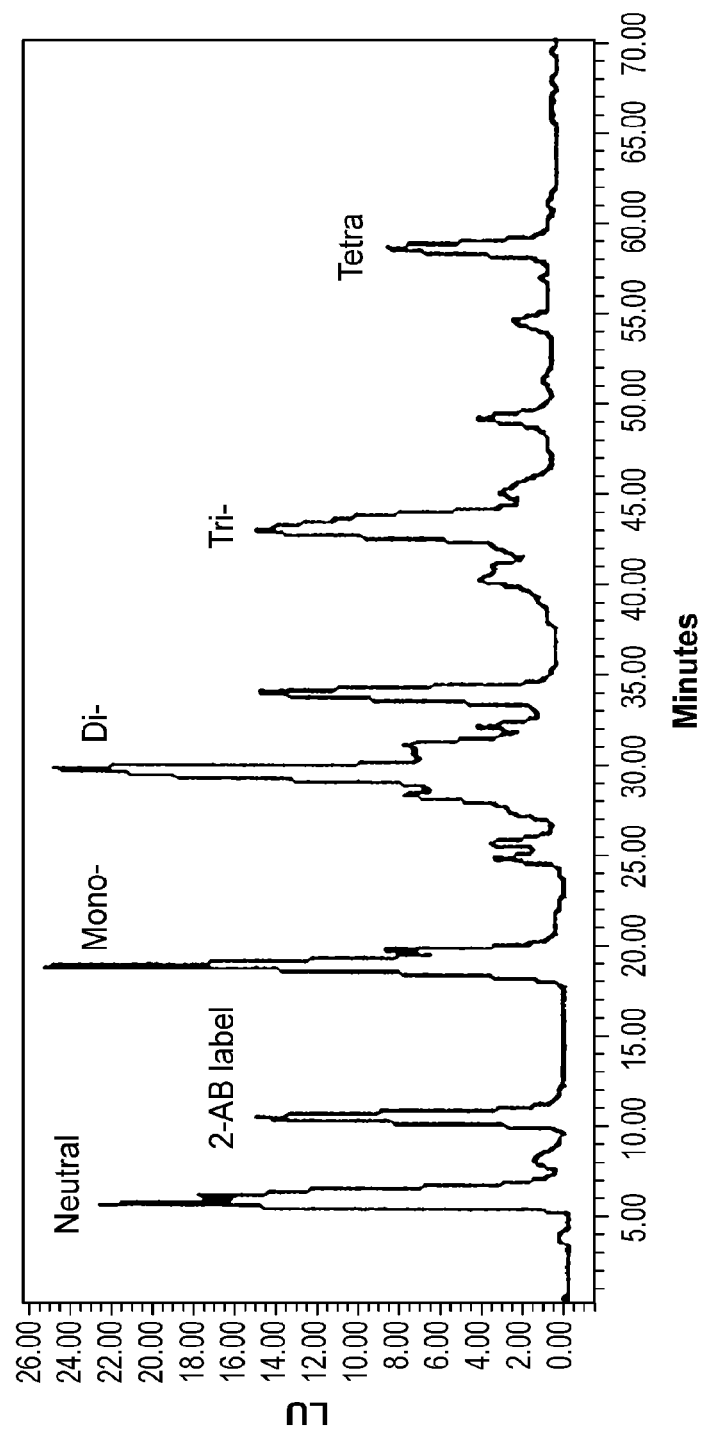
FIG. 1. Representative chromatogram depicting separation of N-glycans by charge via anion exchange chromatography.
Figure 2:
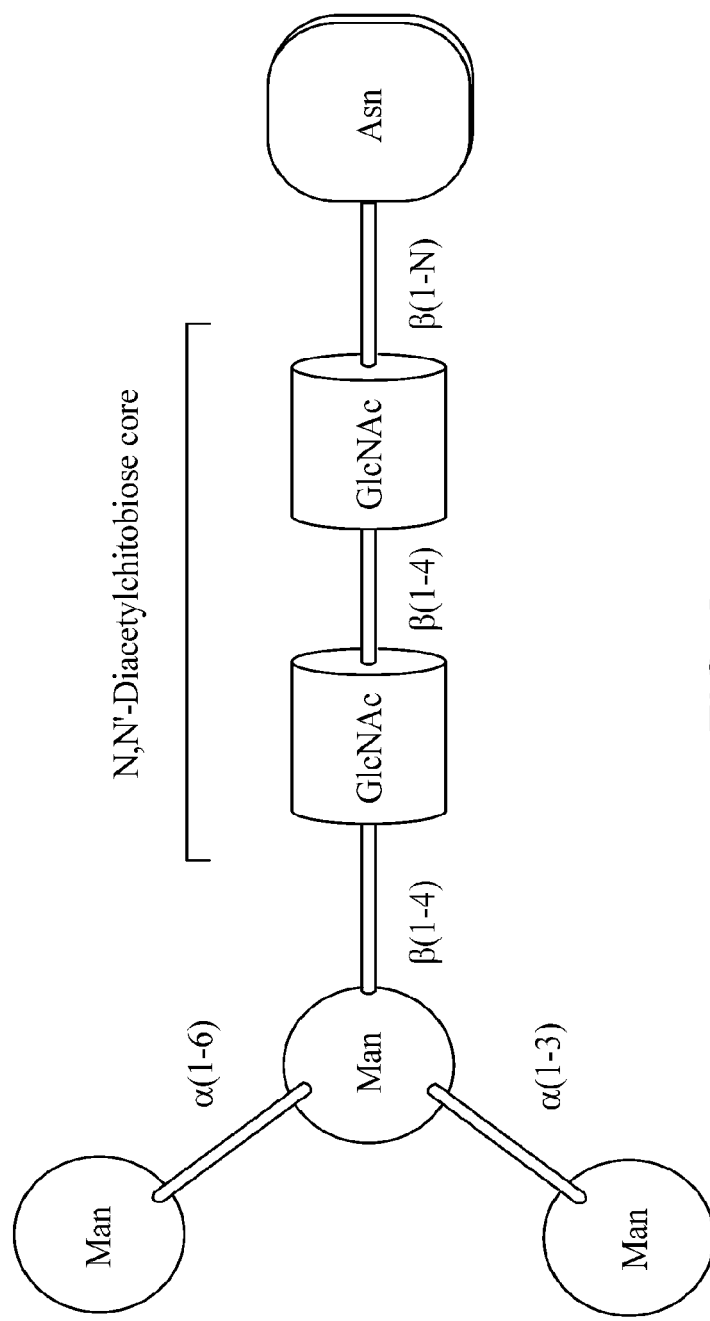
FIG. 2. Common core structure of an N-glycan/N-linked glycan.
Figure 3A:
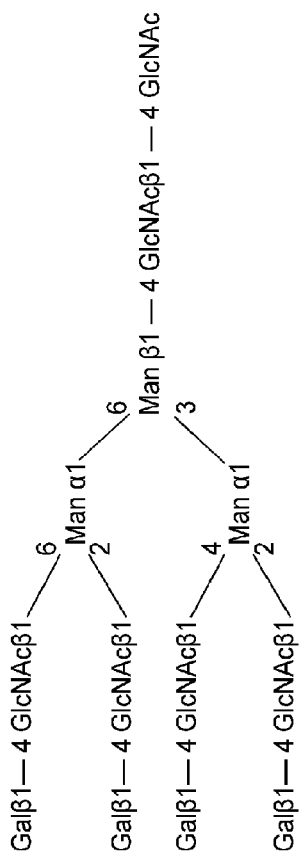
FIGS. 3A-3U. Exemplary N-glycans.
Figure 3B:
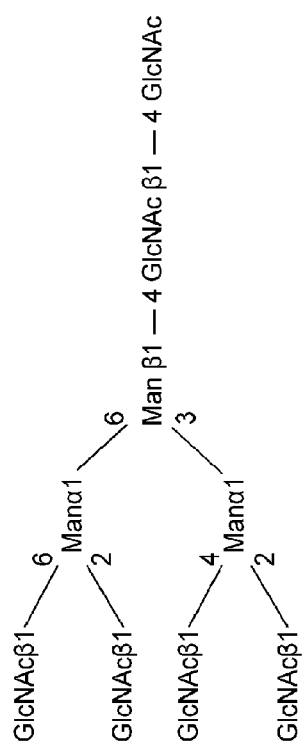
Figure 3E:
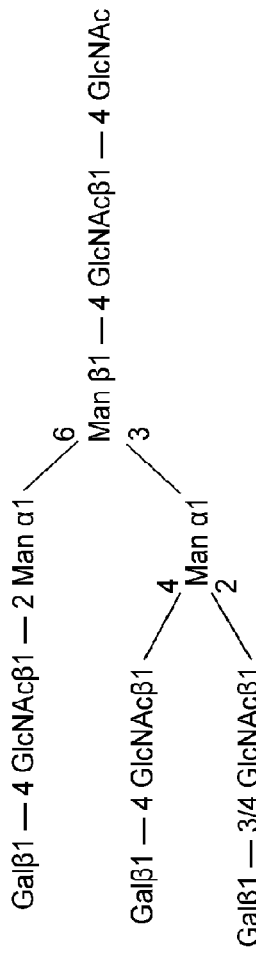
Figure 3F:
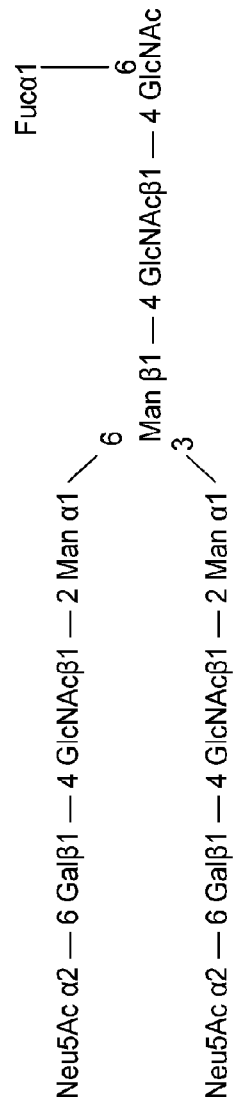
Figure 3G:
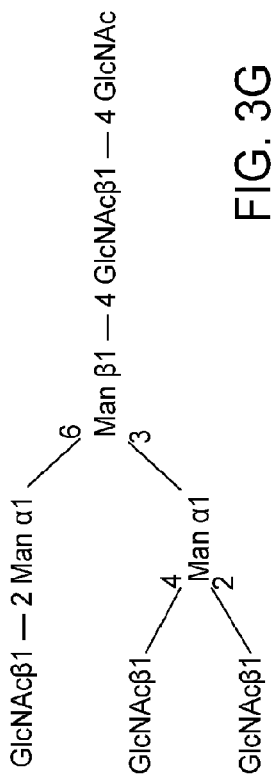
Figure 3H:
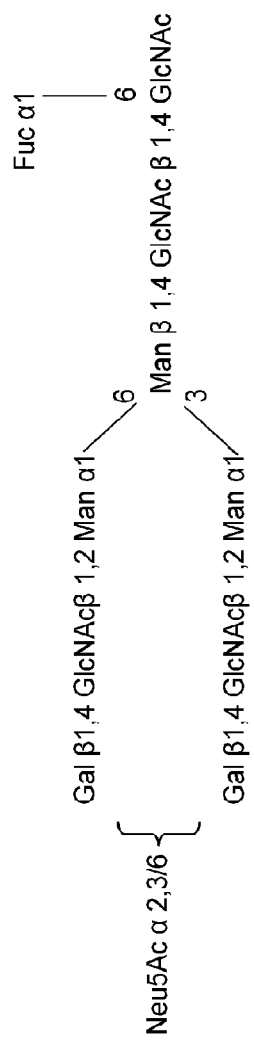
Figure 3I:
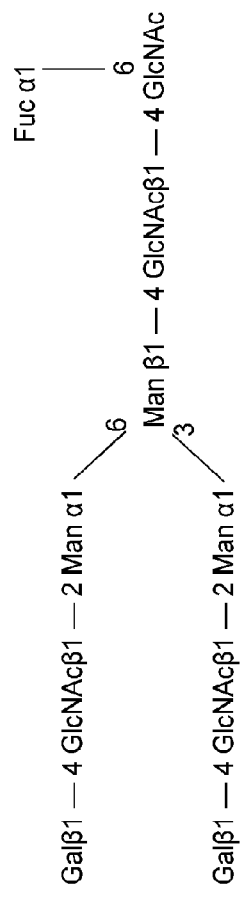
Figure 3J:
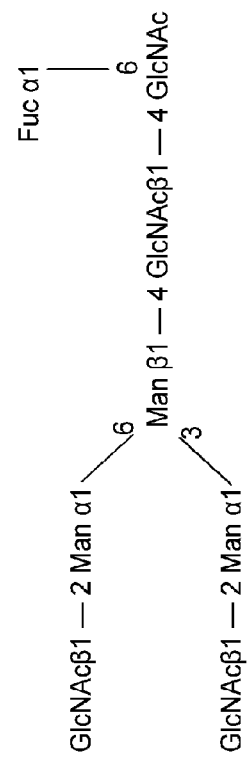
Figure 3M:
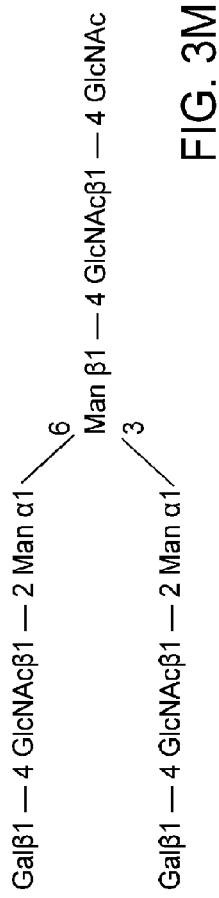
Figure 3N:
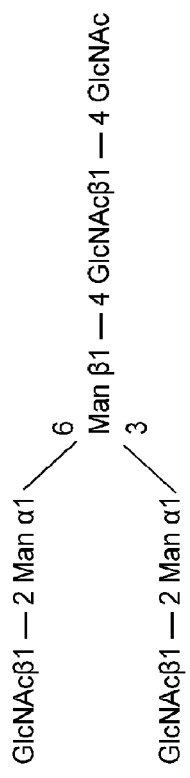
Figure 3O:
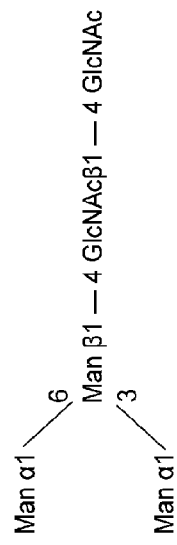
Figure 3P:
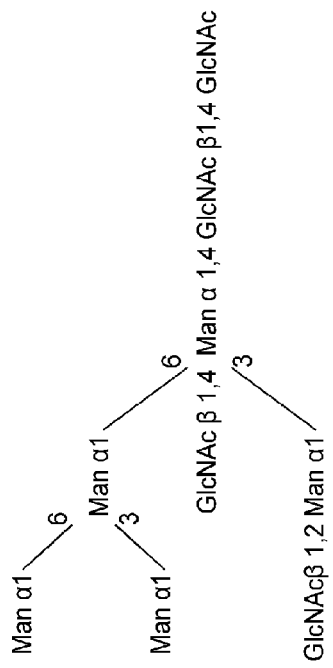
Figure 3S:
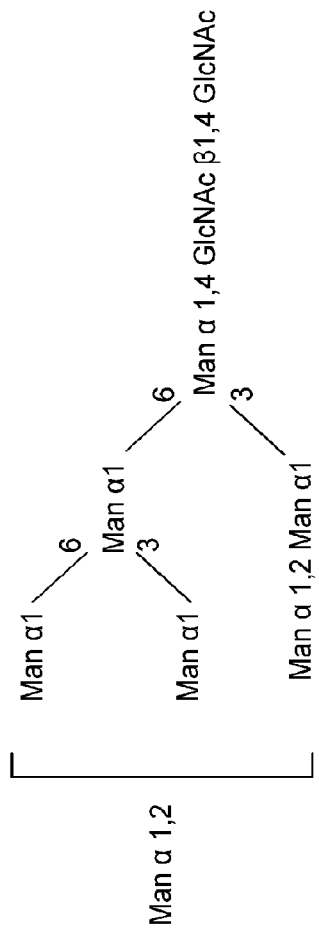
Figure 3T:
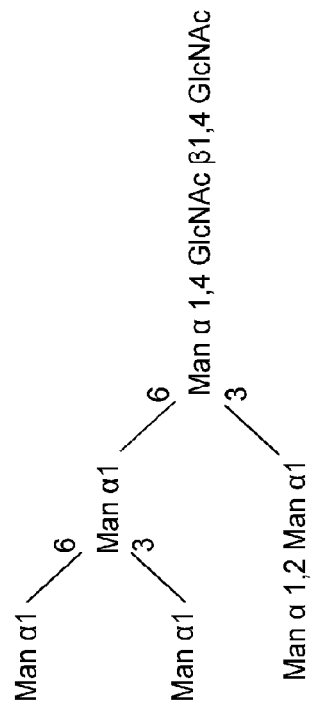
Figure 4B:
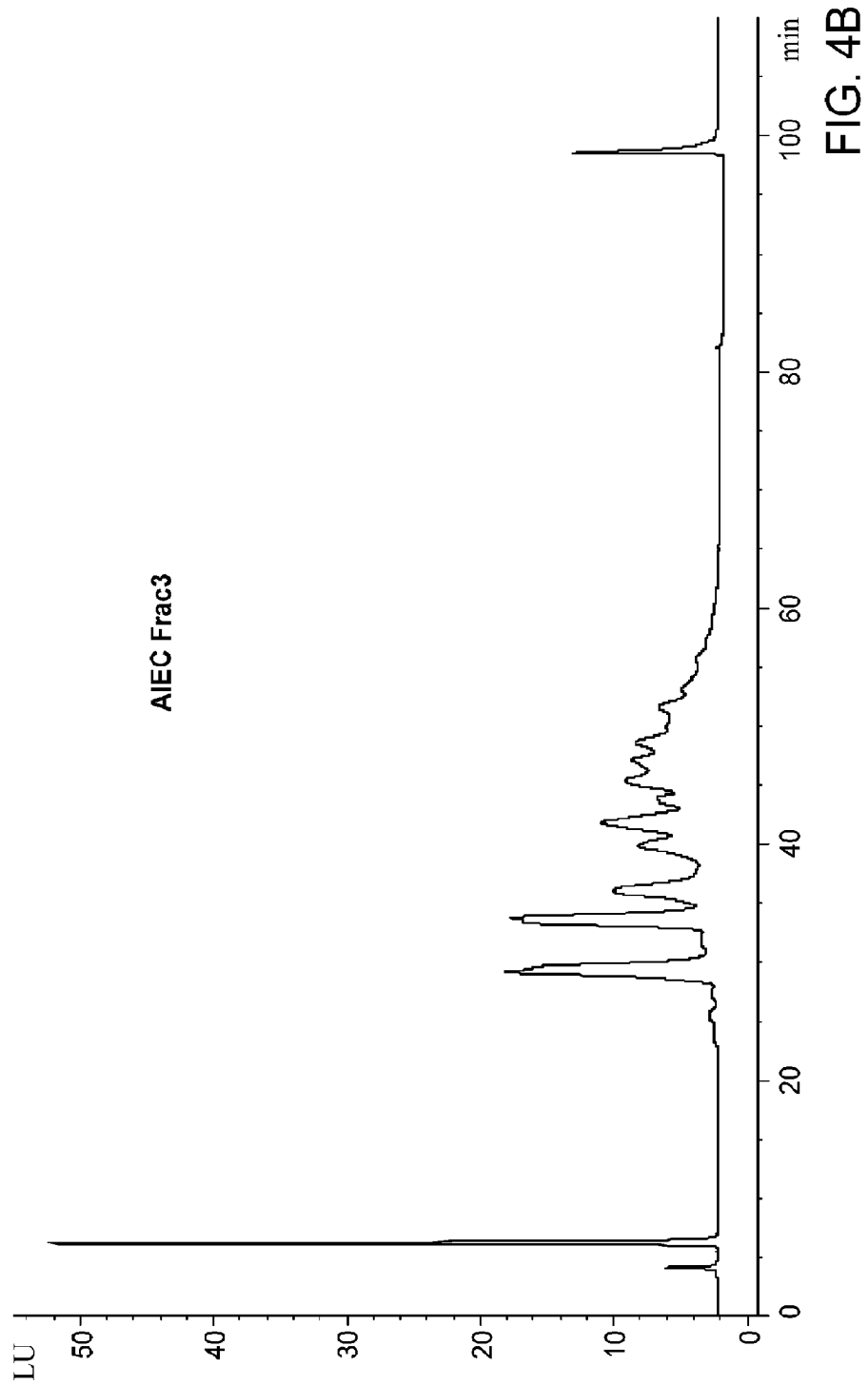
Figure 4C:
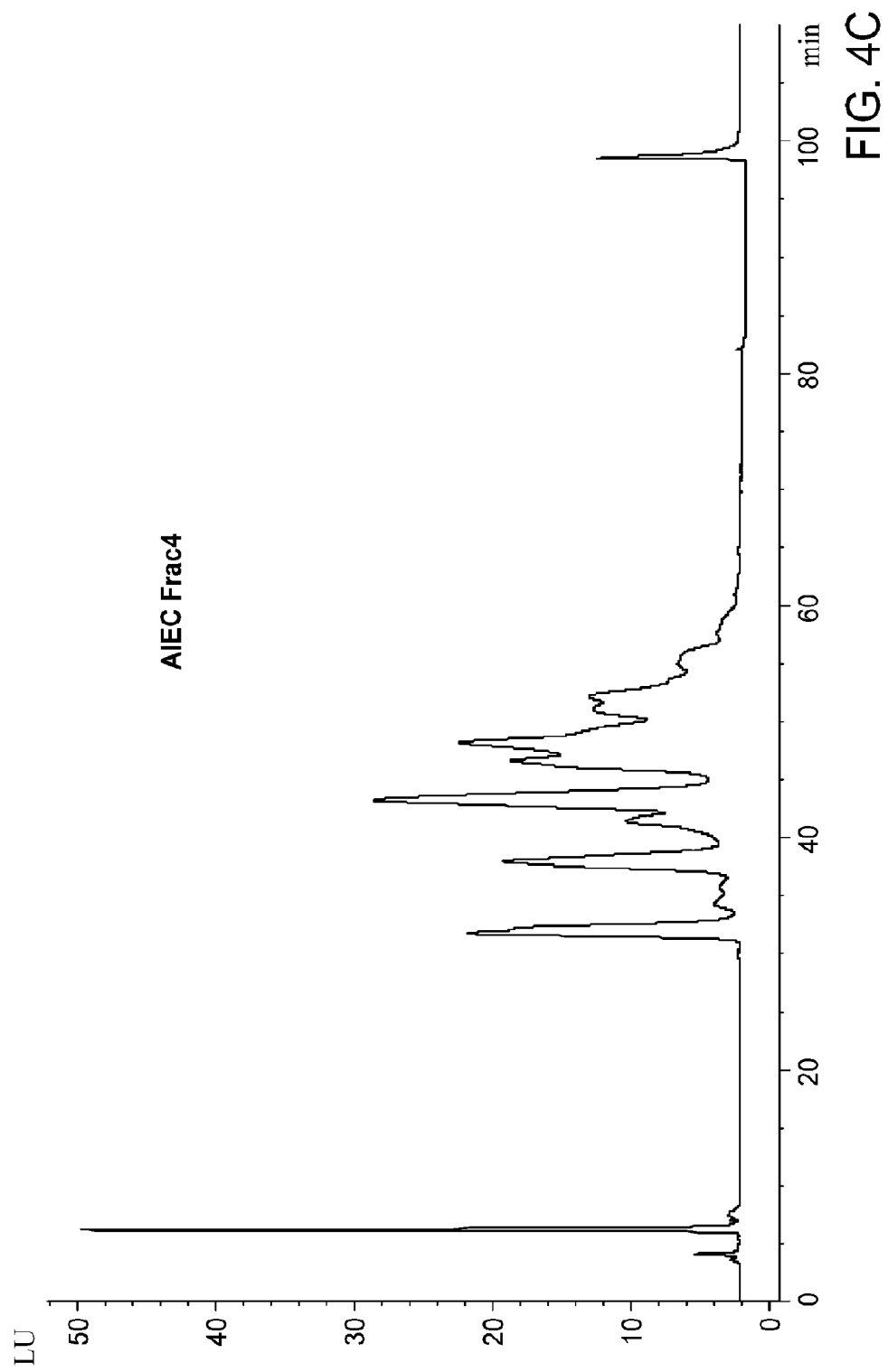
Figure 4D:
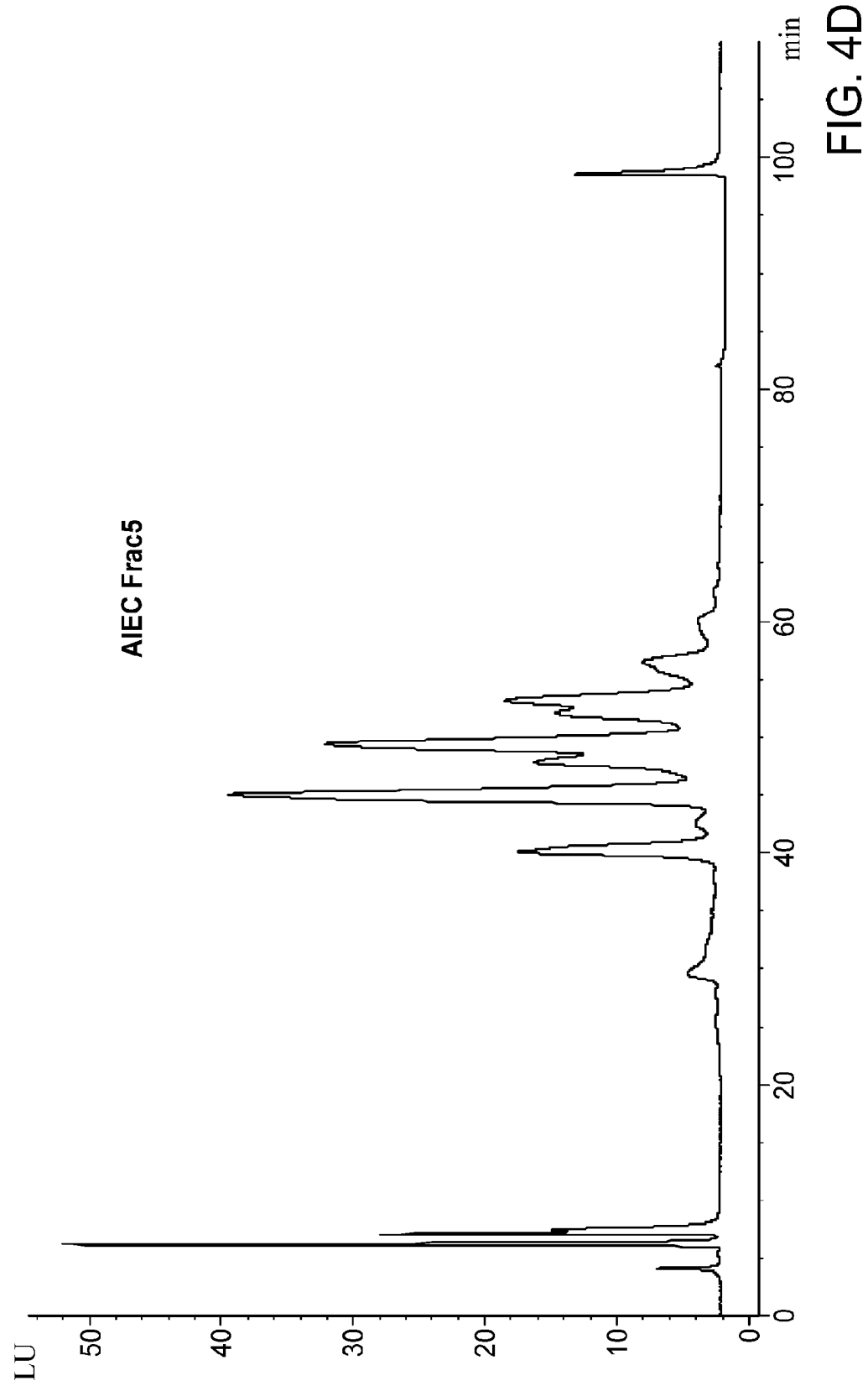
Figure 4E:
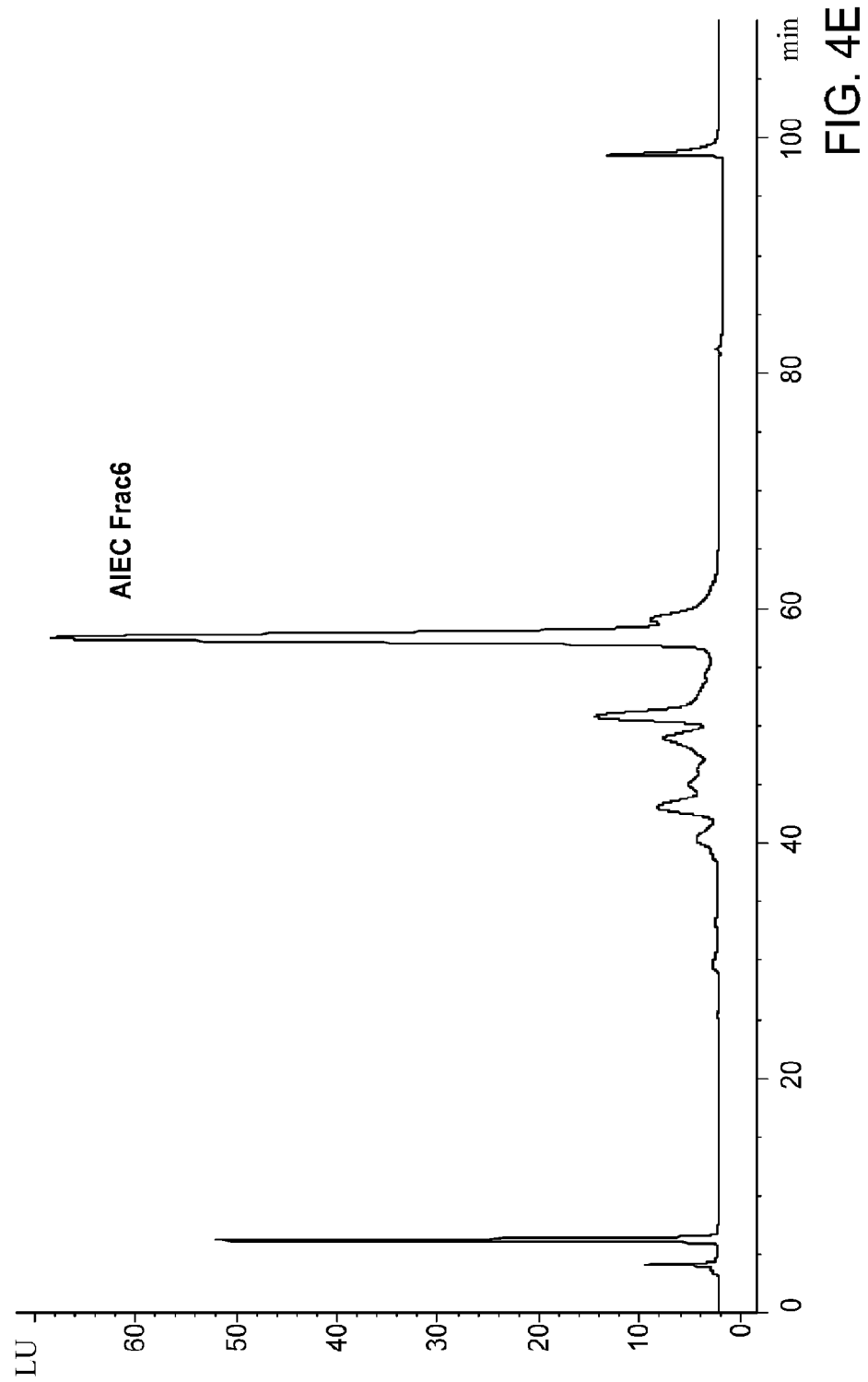
Figure 4F:
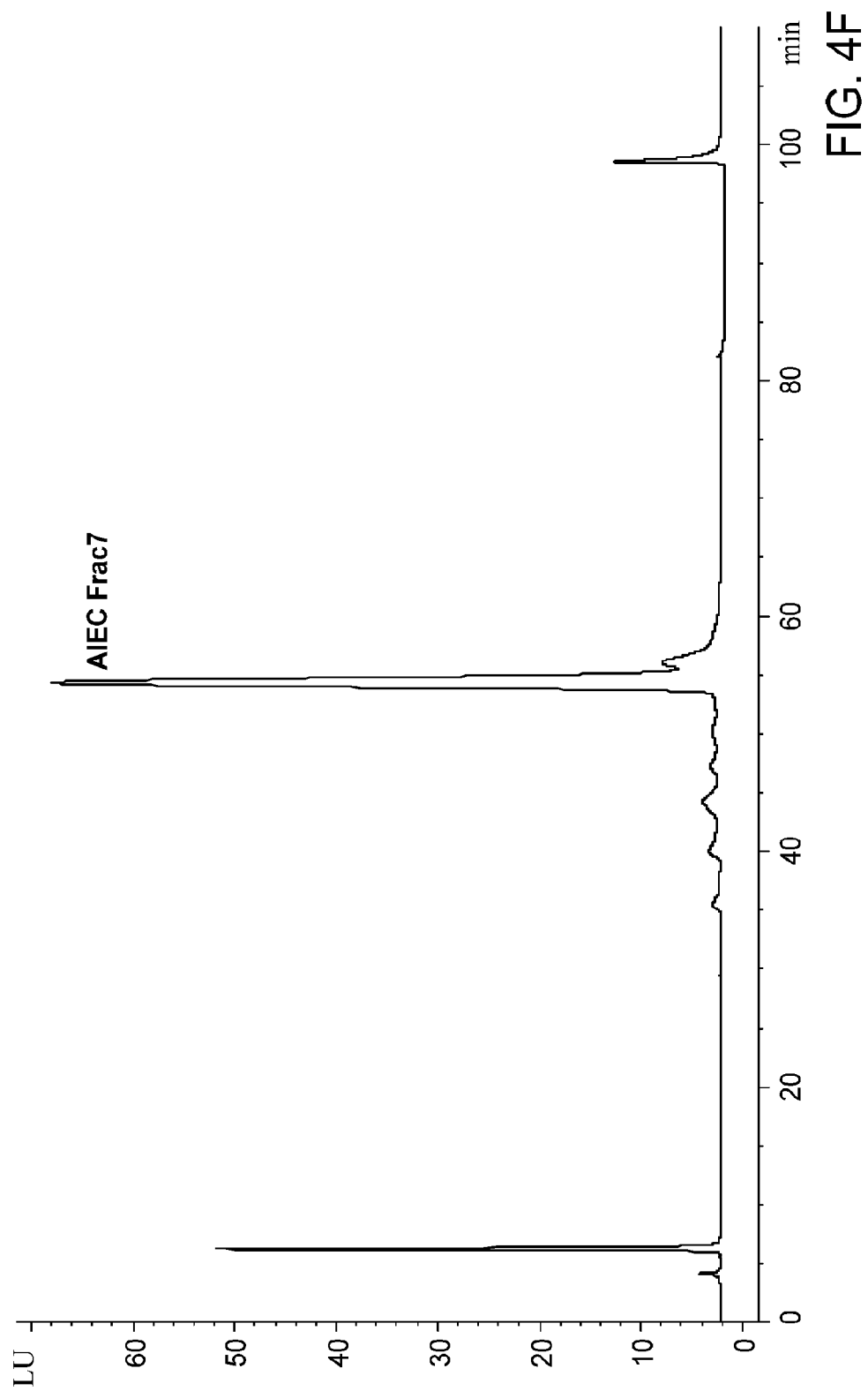
Figure 4G:
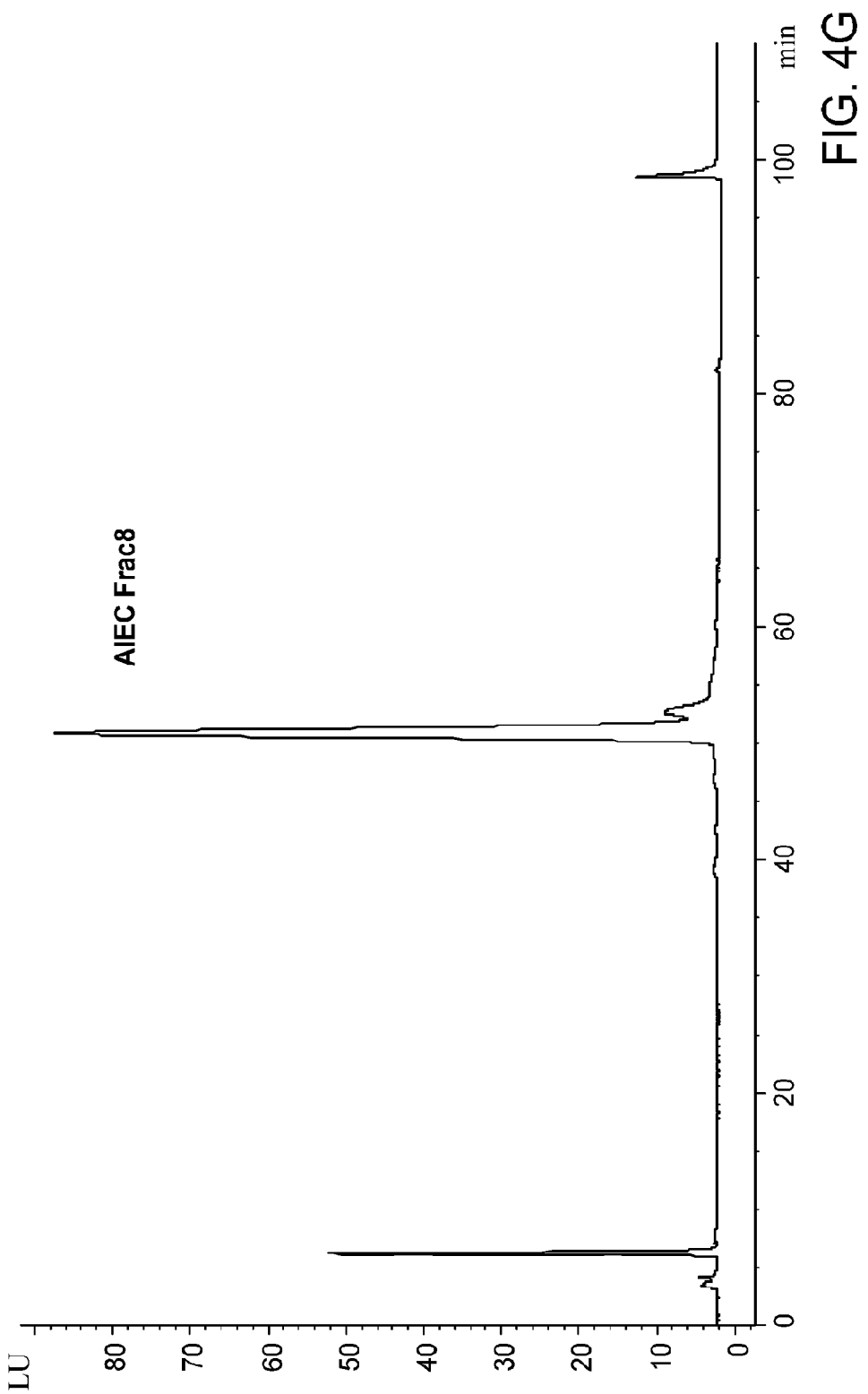
Figure 4H:
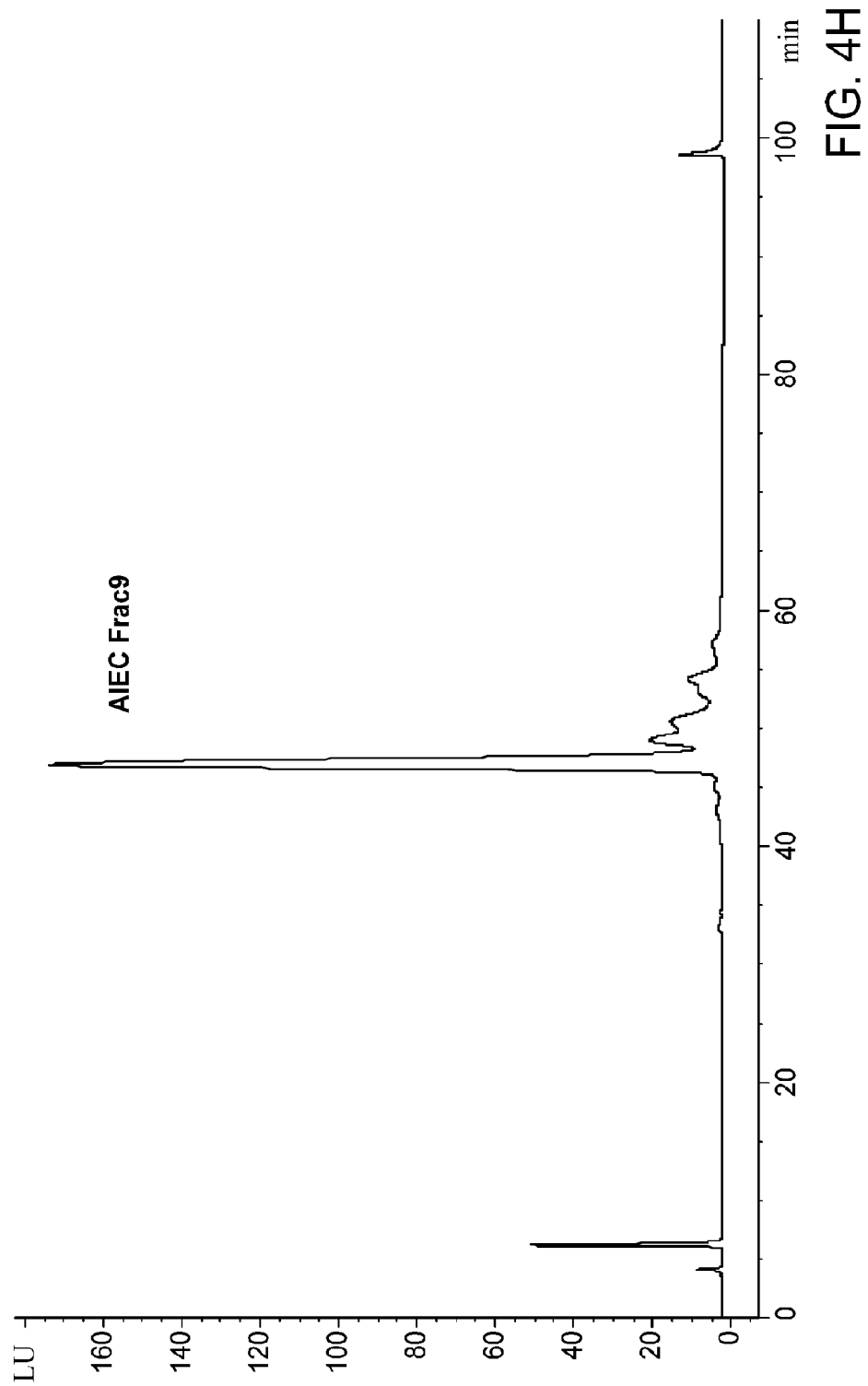
Figure 4I:
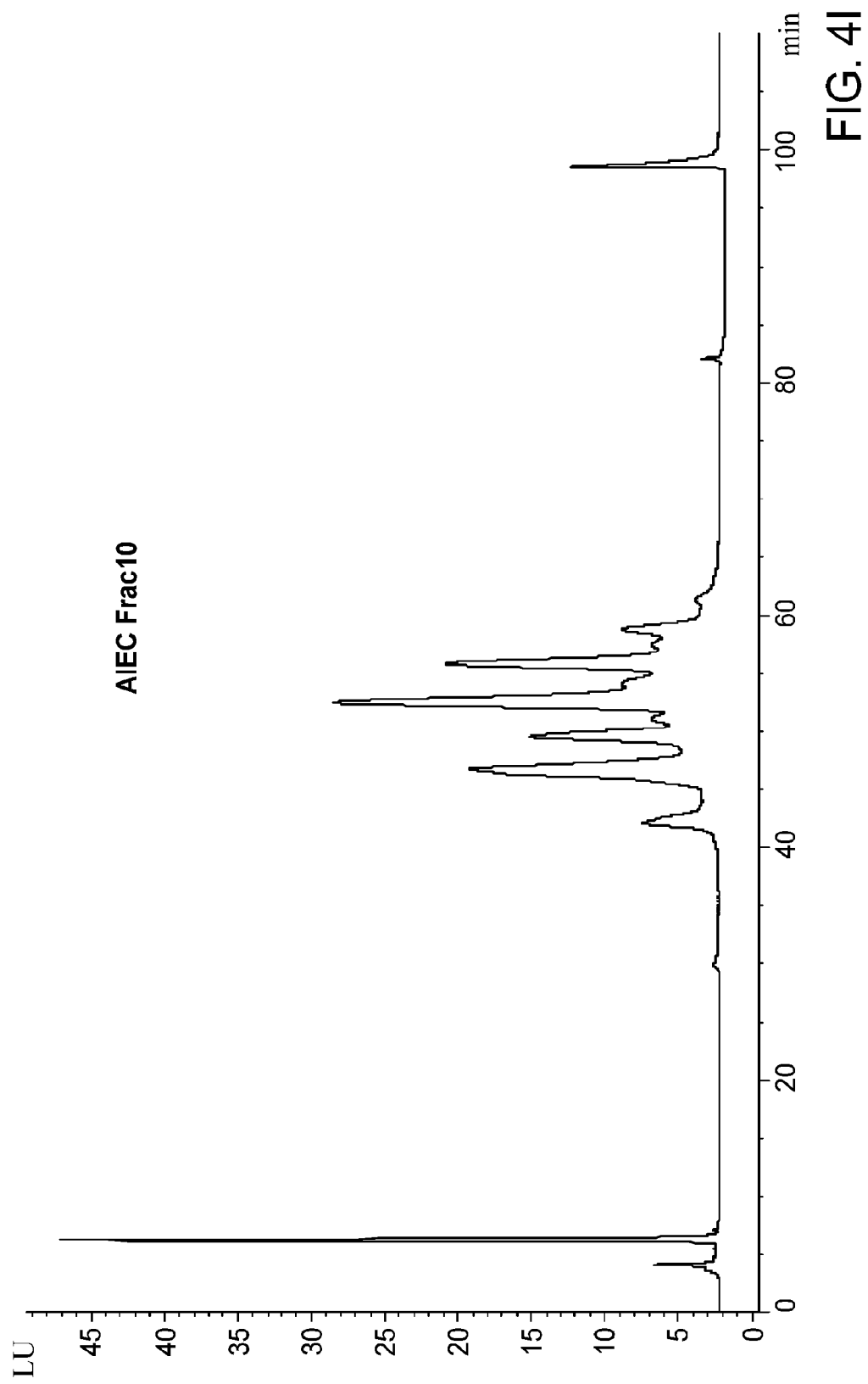
Figure 4J:
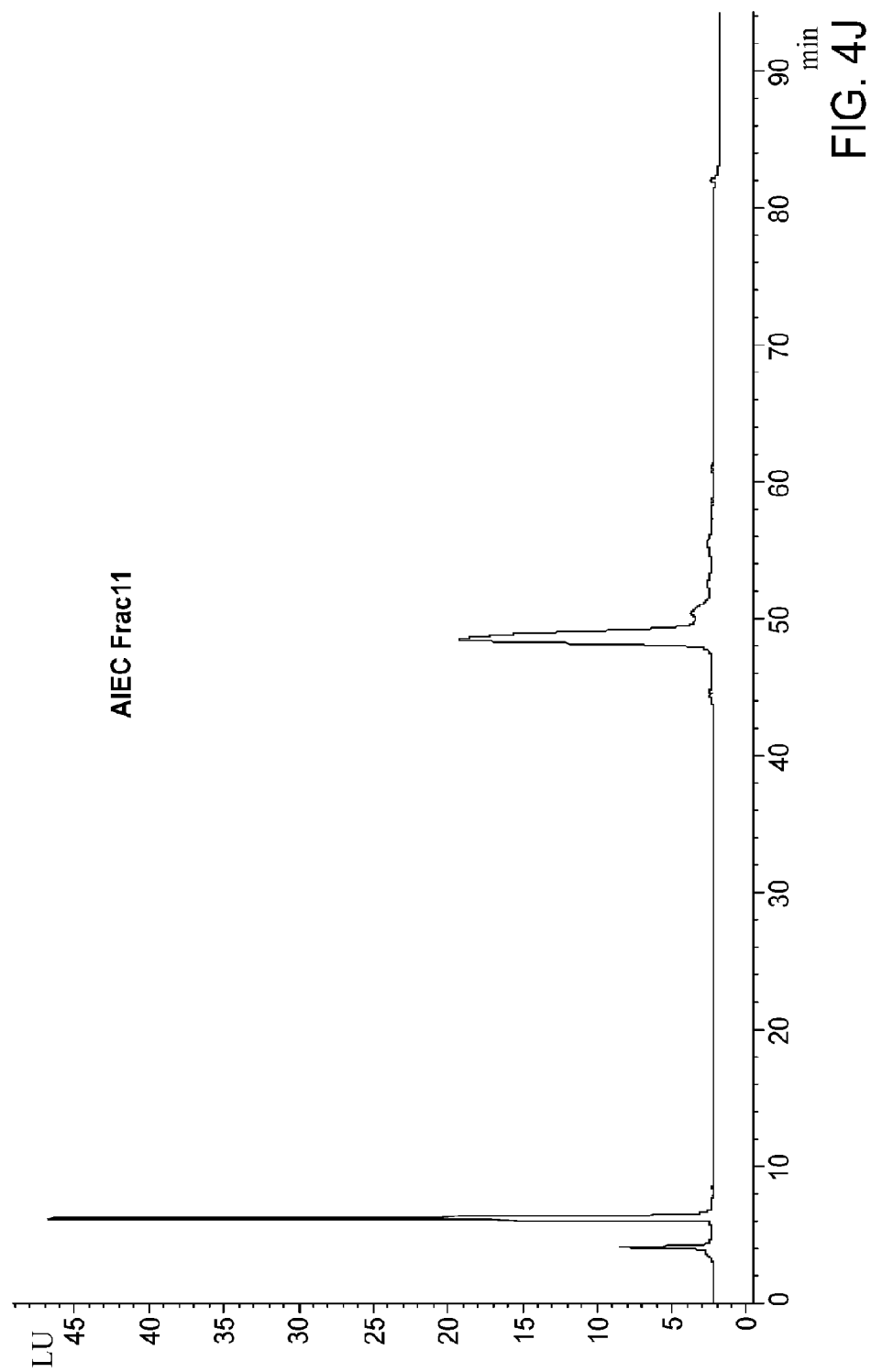

Owing to the complexity of typical glycan pools, we have found that the employment of a single, one-dimensional, separation technique (even at high resolution) may not provide the best resolution of individual N-glycan components. The present disclosure provides multi-dimensional chromatographic methods for the separation of N-glycans.

In certain embodiments, this method is a two-dimensional chromatographic method. In certain embodiments, this method involves more than two separation dimensions. In some aspects, N-glycans are quantified (e.g., in the second dimension) relative to a standard (e.g., a labeled standard).

In one aspect, the disclosure provides multi-dimensional chromatographic methods for the separation of N-glycans, comprising the steps of: (i) providing a glycan preparation, wherein the glycan preparation includes at least one negatively charged N-glycan; and (ii) separating the glycan preparation by anion-exchange chromatography and at least one secondary chromatographic technique.

In certain embodiments, the multi-dimensional chromatographic method effects separation of isomeric N-glycans.

It will be appreciated that the anion-exchange chromatography separation may be performed at any stage during the multi-dimensional chromatographic method. In one embodiment, anion-exchange chromatography is used to perform the initial separation of the glycan preparation (i.e., first dimension). In another embodiment, a different type of chromatography (e.g., any of those discussed herein) can be used for the initial separation of the glycan preparation and anion-exchange chromatography can be used to perform a subsequent secondary separation (e.g., second dimension).

In one aspect, a known quantity of a reference N-glycan can be included in a glycan preparation that is to be separated according to the methods that are described herein. The reference N-glycan can then be used to provide a relative quantification for other glycans in the preparation.

In one embodiment, the reference N-glycan is selected so that it is unlikely to occur naturally in the glycan preparation. This will ensure that the reference N-glycan does not interfere with the analysis. Alternatively, the reference N-glycan can be labeled with a unique label that allows it to be differentiated from other glycans in the glycan preparation that may be labeled with a different label or a collection of different labels. The addition of a known quantity of reference N-glycan to the glycan preparation enables each component of the glycan preparation to be quantified.

Absolute quantitation of N-glycans can be accomplished by spiking the mixture to be analyzed with an appropriate fluorescently-labeled standard. Relative quantitation of N-glycans can be accomplished by comparison of fluorescence peak areas of the species that are resolved by chromatography.

Thus, in certain embodiments, the present disclosure provides a method of characterizing a mixture of N-glycans, said method comprising steps of:

(i) providing a glycan preparation, wherein the glycan preparation includes at least one negatively charged N-glycan and a known quantity of a reference N-glycan, wherein the reference N-glycan is labeled with a labeling agent;

(ii) separating the glycan preparation by anion-exchange chromatography and at least one secondary chromatographic technique; and (iii) quantifying at least one N-glycan in the glycan preparation relative to the reference N-glycan.

Anion-Exchange Chromatography (AIEC)

As discussed above, separation of a glycan preparation is provided in one dimension by anion exchange chromatography (AIEC). In brief, anion exchange chromatography is a chromatographic technique which relies on charge-charge interactions between a negatively charged compound and a positively charged resin.

Exemplary anion exchange resins (i.e., the stationary phase) include, but are not limited to, quaternary amine resins or "Q-resins" (e.g., Q-Sepharose®, QAE Sephadex®); diethylaminoethane (DEAE) resins (e.g., DEAE-Trisacryl®, DEAE Sepharose®, benzoylated naphthoylated DEAE, diethylaminoethyl Sephacel®); Amberjet® resins; Amberlyst® resins; Amberlite® resins (e.g., Amberlite® IRA-67, Amberlite® strongly basic, Amberlite® weakly basic), cholestyramine resin, ProPac® resins (e.g., ProPac® SAX-10, ProPac® WAX-10, ProPac® WCX-10); TSK-GEL® resins (e.g., TSKgel DEAE-NPR; TSKgel DEAE-5PW); and Acclaim® resins. In certain embodiments, the anion exchange resin is a Q resin. In certain embodiments, the anion exchange resin is a DEAE resin. In certain embodiments, the DEAE resin is a TSK-GEL® DEAE resin.

Typical mobile phases for anionic exchange chromatography include relatively polar solutions, such as water and polar organic solvents (e.g., acetonitrile and organic alcohols such as methanol, ethanol, and isopropanol). Thus, in certain embodiments, the mobile phase comprises about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% actetonitrile. In certain embodiments, the mobile phase comprises between about 1% to about 100%, about 5% to about 95%, about 10% to about 90%, about 20% to about 80%, about 30% to about 70%, or about 40% to about 60% acetonitrile at any given time during the course of the separation.

In certain embodiments, the mobile phase is buffered. In certain embodiments, the mobile phase is not buffered. In certain embodiments, the mobile phase is buffered to a pH between about 7 to about 14. In certain embodiments, the mobile phase is buffered to a pH between about 7 to about 10. In certain embodiments, the mobile phase is buffered to a pH between about 7 to about 8. In certain embodiments, the mobile phase is buffered to a pH of about 7.

Exemplary buffers for anion exchange chromatography are included in Table 2.

TABLE 2

Buffers for anion exchange chromatography

| Molecule | pKa | dpKa/degree C. | Counter ion |
|---|---|---|---|
| Ammonium (NH$_4$) | | | chloride, bromide iodide, acetate |
| N-methyl piperazine | 4.75 | −0.015 | chloride |
| piperazine | 5.68 | −0.015 | chloride or formate |
| L-histidine | 5.96 | | chloride |
| bis-Tris | 6.46 | −0.017 | chloride |
| bis-Tris propane | 6.80 | | chloride |
| triethanolamine | 7.76 | −0.020 | chloride or acetate |
| Tris | 8.06 | −0.028 | chloride |
| N-methyl-diethanolamine | 8.52 | −0.028 | chloride |
| diethanolamine | 8.88 | −0.025 | chloride |
| 1,3-diaminopropane | 8.64 | −0.031 | chloride |
| ethanolamine | 9.50 | −0.029 | chloride |
| piperazine | 9.73 | −0.026 | chloride |
| 1,3-diaminopropane | 10.47 | −0.026 | chloride |
| piperidine | 11.12 | −0.031 | chloride |
| phosphate | 12.33 | −0.026 | chloride |

In certain embodiments, the buffer is selected from a group consisting of ammonia, ammonium chloride, ammonium acetate, ammonium formate, ammonium phosphate, ammonium carbonate, ammonium bicarbonate, N-methyl piperazine, piperazine, piperadine, L-histidine, Tris, bis-Tris, bis-Tris propane, triethanolamine, N-methyl-diethanolamine, diethanolamine, 1,3-diaminopropane, ethanolamine, and phosphate buffers. In certain embodiments, the buffer is ammonium acetate. In certain embodiments, the buffer is ammonium chloride. In certain embodiments, the buffer is ammonium formate. In certain embodiments, the buffer is ammonium phosphate. In certain embodiments, the buffer is ammonium carbonate. In certain embodiments, the buffer is ammonium bicarbonate.

In certain embodiments, the temperature of the anion exchange column (which houses the resin) is between about 10° C. and about 50° C. In certain embodiments, the temperature of the anion exchange column is between about 20° C. and about 50° C. In certain embodiments, the temperature of the anion exchange column is between about 30° C. and about 50° C. In certain embodiments, the temperature of the anion exchange column is about 40° C.

The column can be maintained at a constant temperature throughout the separation, e.g., using a commercial column heater. In some embodiments, the column can be maintained at a temperature from about 18° C. to about 45° C., e.g., about 18° C., 20° C., 22° C., 25° C., 30° C., 37° C., 40° C. or 45° C. In certain embodiments, for consideration of glycan stability, the column temperature is not set higher than 45° C.

Other Chromatographic Techniques

The multi-chromatographic method of the present disclosure also provides for separation of the glycan preparation by at least one secondary chromatographic technique in addition to anion exchange chromatography.

In certain embodiments, this step may sequentially employ two, three, four, or more, different secondary chromatographic techniques. In certain embodiments, the methods employ one secondary chromatographic technique. In certain embodiments, the methods employ two different secondary chromatographic techniques. In certain embodiments, the methods employ three different secondary chromatographic techniques. In certain embodiments, the methods employ one to three different secondary chromatographic techniques. It is also to be understood that the same chromatographic technique may be used several times during a single separation (e.g., with a slightly different column, different eluting conditions, etc.).

Secondary techniques that can be used according to the methods described herein include, but are not limited to, reverse phase liquid chromatography (RP and RP-HPLC), normal phase liquid chromatography (NP and NP-HPLC), ion-pairing reverse phase chromatography (IP-RP and IPRP-HPLC), size exclusion chromatography, affinity chromatography (AC and AC-HPLC), capillary electrophoresis (CE); fluorophore-assisted carbohydrate electrophoresis (FACE); electrochromatography, and micellar electrokinetic chromatography (MEKC). Each of these is described in more detail below.

In certain embodiments, the secondary chromatographic technique is or includes reverse phase liquid chromatography. Reverse phase liquid chromatography (RP) is a chromatographic technique which relies on differences in polarity between a (non-charged) polar analyte and a (non-charged) non-polar resin. The driving force in the binding of the analyte to the stationary phase is the decrease in the area of the non-polar segment of the analyte exposed to the solvent. This hydrophobic effect is dominated by the decrease in free energy from entropy associated with the minimization of the ordered analyte-polar solvent interface. The hydrophobic effect is decreased by adding more non-polar solvent into the mobile phase. This shifts the partition coefficient such that the analyte spends some portion of time moving down the column in the mobile phase, eventually eluting from the column. The characteristics of the analyte play an important role in its retention characteristics. In general, an analyte with a longer alkyl chain length results in a longer retention time because it increases the analyte's hydrophobicity. Very large analytes, however, can result in incomplete interaction between the large analyte surface and the alkyl chain. Retention time increases with hydrophobic surface area which is roughly inversely proportional to analyte size. Branched chain analytes elute more rapidly than their corresponding isomers because the overall surface area is decreased.

Stationary phases for reverse phase chromatography include, but are not limited to, silylated silica (i.e., wherein silica has been treated with $RMe_2SiCl$, and wherein R is a straight chain alkyl group such as $C_{18}H_{37}$, $C_8H_{17}$, or $C_4H_7$), diphenyl resins, divinylbenzene resins, and carbon resins.

The designations for the $RMe_2SiCl$ reversed phase materials refer to the length of the hydrocarbon chain. In certain embodiments, reverse phase chromatography may include the use of a C18 reverse phase resin (e.g., for example, octadecylsilane or octadecylsilica, a.k.a. ODS), C8 reverse phase resin, or a C4 reverse phase resin. However, in certain embodiments, use of an ODS column as the secondary chromatographic technique is specifically excluded.

In certain embodiments, reverse phase chromatography includes the use of a graphitized-carbon resin (e.g., porous graphitized carbon, PGC)

Typical mobile phases for reverse phase chromatography include relatively polar solutions, such as water and polar organic solvents (e.g., acetonitrile, organic alcohols), and may or may not include a buffer. In certain embodiments, the reverse phase technique does not include a buffer. In certain embodiments, the reverse phase technique does include a buffer. Retention time is increased by the addition of polar solvent to the mobile phase and decreased by the addition of more hydrophobic solvent. The retention time is therefore longer for analytes which are more non-polar in nature, allowing polar analytes to elute more readily.

Aside from mobile phase polarity, other mobile phase modifiers can affect analyte retention. For example, the addition of inorganic salts causes a linear increase in the surface tension of aqueous solutions, and because the entropy of the analyte-solvent interface is controlled by surface tension, the addition of salts tend to increase the retention time. Another important component is pH since this can change the hydrophobicity of the analyte. For this reason most methods use a buffering agent, such as sodium phosphate to control the pH. An organic acid such as formic acid or most commonly trifluoroacetic acid is often added to the mobile phase. These serve multiple purposes by controlling the pH, neutralizing the charge on any residual exposed silica on the stationary phase and acting as ion pairing agents to neutralize charge on the analyte. The effect varies depending on use but generally improves the chromatography.

In certain embodiments, reverse phase chromatography may include use of an ion-pair reagent. For example, in ion-pairing reverse phase chromatography (IP-RP) a reverse phase resin is used with a stationary phase which includes an ion pair reagent (e.g., ion pair of an acid and a base) as an additive. When used with common hydrophobic stationary phases in the reversed-phase mode, ion pair reagents can be used to selectively increase the retention of charged analytes, and enhance peak shape and retention time when common remedies such as modifying eluent ratios or changing stationary phase fail. Exemplary ion-pair reagents include: combinations of acids and bases, such as acetic acid and an organic amine (e.g., dibutylamine); N-hydroxytetrabutylamine; N-hydroxytriethyldodecylamine; and the like. In other embodiments of this method, an ion-pair reagent may be selected from the following list: cethexonium bromide, triethylamine, tributylamine, tripentylamine, tetrabutyl ammonium bromide, tetrabutyl ammonium chloride, tetrabutyl ammonium dihydrogen phosphate, tetrabutyl ammonium hydrogen sulfate, tetrabutyl ammonium hydroxide, tetrabutyl ammonium iodide, tetrabutyl phosphonium bromide, tetrabutyl phosphonium hydrogen sulfate, tetradecyl trimethyl ammonium bromide, tetradecyl trimethyl ammonium hydrogensulfate, tetraethyl ammonium bromide, tetraethyl ammonium hydrogen sulfate, tetraethyl ammonium hydroxide, tetraheptyl ammonium bromide, tetrahexylammonium bromide, tetrahexyl ammonium dihydrogen phosphate, tetrahexyl ammonium hydrogen sulfate, tetramethyl ammonium bromide, tetramethyl ammonium hydrogen sulfate, tetramethyl ammonium hydroxide, tetramethyl ammonium sulfate, tetraoctyl ammonium bromide, tetrapentyl ammonium bromide, tetrapropyl ammonium bromide, tetrapropyl ammonium hydrogen sulfate, or tetrapropyl ammonium hydroxide.

In certain embodiments, the secondary chromatographic technique is or includes normal phase liquid chromatography. Normal phase liquid chromatography (NP) is a chromatographic technique which relies on differences in polarity between a (non-charged) non-polar analyte and a (non-charged) polar resin. Polar analytes associate with and are retained by the polar stationary phase. Adsorption strengths increase with increase in analyte polarity, and the interaction between polar analytes and the polar stationary phase (relative to the mobile phase) increases the elution time. The interaction strength not only depends on the functional groups in the analyte, but also on steric factors and structural isomers are often resolved from one another. Stationary phases for normal phase chromatography include, but are not limited to, silica gel (silanol), alumina, Fluorisil®, and modified silica gels (e.g., such as cyano-modified silica gel; amine-modified silica gel, and amide-modified silica gel). In certain embodiments, normal phase chromatography includes the use of modified silica gel. In certain embodiments, modified silica gel includes cyano-modified silica gel, amine-modified silica gel, or amide-modified silica gel. In certain embodiments, the amide-modified silica gel is GlycoSep-N.

A typical mobile phase normal phase chromatography includes non-polar organic solvents such as hydrocarbons (e.g., hexanes, pentanes, cyclohexane), halogenated hydrocarbons (e.g., dichloromethane, chloroform, dichloroethane), aromatic hydrocarbons (e.g., benzene, toluene, xylenes), aromatic halogenated hydrocarbons (e.g., chlorobenzene), ethers (e.g., tetrahydrofuran, diethylether), esters (e.g., ethyl acetate, isopropylacetate), or mixtures thereof. Organic alcohols (e.g., methanol, ethanol, isopropanol, t-butanol) or other polar solvents (e.g., acetonitrile) may be added to the eluting solution in minor amounts in order to increase overall solvent polarity, and decrease the retention time of the analytes; more hydrophobic solvents tend to increase retention times. Organic bases (e.g., triethylamine, diisopropylethyl amine) may also be used in minor amounts to the mobile phase in order to neutralize the slight acidity of the silica gel, and decrease the retention time of basic analytes. Water as a component of the mobile phase in NP chromatography is excluded.

In certain embodiments, the normal phase chromatography step may be performed in an aqueous normal phase (ANP) format which encompasses the mobile phase region between reversed-phase chromatography (RP) and organic normal phase chromatography (ONP). Water must be present in the mobile phase in order to permit the partitioning of solutes in a "normal phase" order. Mobile phases for ANP are based on an polar organic solvent (e.g., an organic alcohol, acetonitrile) with a small amount of water; thus, the mobile phase is both "aqueous" (water is present) and "normal" (less polar than the stationary phase). Thus, polar analytes (such as acids and amines) are most strongly retained, with retention decreasing as the amount of water in the mobile phase increases. Generally, the amount of the nonpolar component in the mobile phase must be approximately 50% or greater with the exact point of increased retention depending on the analyte and the organic component of the mobile phase. A true ANP stationary phase will be able to function in both the reversed phase and normal phase modes with only the amount of water in the eluent varying. Thus a continuum of solvents can be used from 100% aqueous to pure organic.

ANP retention has been demonstrated for a variety of polar compounds on the hydride based stationary phases (see, for example, Pesek and Matyska, *Journal of Separation Science* (2005) 28:2437-2443; Pesek and Matyska, *LCGC* (2006) 24:296; Pesek et al., *Journal of Separation Science* 29: 872-880 (2006)). An interesting feature of these phases is that both polar and nonpolar analytes can be retained over some range of mobile phase composition (organic/aqueous) as a result of residual silanol groups acting in a HILIC (hydrophilic interaction chromatography) mode. This property distinguishes it from a pure HILIC column where separation by polar differences is obtained, or a pure RP stationary phase on which separation by non-polar differences in analytes is obtained with very limited secondary mechanisms operating. Another important feature of the hydride-based phases is that for many analyses it is usually not necessary to use a high pH mobile phase to analyze polar analytes such as bases. The aqueous component of the mobile phase usually contains from 0.1 to 0.5% formic, acetic acid, or trifluoroacetic acid, which is compatible with detector techniques that include mass spectral analysis.

In certain embodiments, the secondary chromatographic technique is or includes size exclusion chromatography. Size exclusion chromatography (SEC) also known as gel permeation chromatography or gel filtration chromatography is a chromatographic technique which separates the components of a mixture on the basis of size. This typically involves passing the mixture through a material with narrow pores that restrict the passage of different components to different extents.

In certain embodiments, the secondary chromatographic technique is or includes affinity chromatography. Affinity chromatography (AC) is a chromatographic technique which relies on the property of biologically active substances to form stable, specific, and reversible complexes. The formation of these complexes involves the participation of a combination of common molecular forces such as the van der Waal's interactions, electrostatic interactions, dipole-dipole interactions, hydrophobic interactions, and hydrogen bonding. An efficient, biospecific bond is formed by a simultaneous and concerted action of several of these forces in the complementary binding sites. For example, a column with conjugated antibodies or lectins against a particular glycan type can be used to preferentially isolate glycans of that type from the remainder of the mixture. In another embodiment, the use of an immobilized metal affinity (IMAC) column can be used, to preferentially isolate glycans of a structural subtype which will bind to the IMAC resin.

In certain embodiments, the secondary chromatographic technique is or includes capillary electrophoresis. Capillary electrophoresis (CE) is a separation technique which separates ionic analytes by their charge and frictional forces. In traditional electrophoresis, electrically charged analytes move in a conductive liquid medium (stationary phase) under the influence of an electric field. Separations in a capillary electrophoresis system are typically dependent on the analytes having different electrophoretic mobilities (e.g., separation based on on size to charge ratio). However, some classes of analyte cannot be separated by this effect because they are neutral (uncharged) or because they may not differ significantly in electrophoretic mobility. Adding a surfactant to the electrolyte can facilitate the separation of neutral compounds (micellar electrokinetic chromatography, see below). Charged polymers can be separated by filling the capillary with a gel matrix that retards longer strands more than shorter strands (capillary gel electrophoresis). Some capillary electrophoresis systems can also be used for microscale liquid chromatography or capillary electrochromatography.

In certain embodiments, the secondary chromatographic technique is or includes fluorophore-assisted carbohydrate electrophoresis (FACE) in which the glycans are labeled with a fluorophore to facilitate detection (see, for example, Gao and Lehrman, *Glycobiology* (2003) 13:1 G-3G). Terminal aldehydes of N-glycan residues released by hydrolysis may be tagged with charged fluorophores (e.g., 8-aminonaphthalene-1,3,6-trisulfonate (ANTS); 8-aminopyrene-1,3,6-trisulfonic acid (APTS); 2-aminobenzoic acid (2AA); 3-aminobenzoic acid (3AA); 4-aminobenzoic acid (4AA); etc.) and separated by electrophoresis (e.g., gel electrophoresis, capillary electrophoresis) based on charge and frictional forces. Other fluorescent labeling agents may be employable by FACE such as, for example, anthranilic acid (AA); 2-aminopyridine (2AP); 2-aminobenzamide (2AB); 3-aminobenzamide (3AB); 4-aminobenzamide (4AB); 2-aminobenzoic ethyl etser (2ABEE); 3-aminobenzoic ethyl etser (3ABEE); 4-aminobenzoic ethyl etser (4ABEE); 2-aminobenzonitrile (2ABN); 3-aminobenzonitrile (3ABN); 4-aminobenzonitrile (4ABN); 3-(acetylamino)-6-aminoacridin (AA-AC); 2-aminoacridone (AMAC); methylanthranilate (MA); 6-aminoquinoline (6AQ); 2-aminonaphthalene-1,3,6-trisulfonate (ANT); 7-aminomethyl-coumarin (AMC); 2-amino(6-amido-biotinyl)pyridine (BAP); 9-fluorenylmethoxy-carbonyl-hydrazide (FMOC-hydrazide); 3,5-dimethylanthranilic acid; 2-amino-4,5-dimethoxy-benzoic acid; 1,2-diamino-4,5-methylenedioxy-benzene (DMB); and ortho-phenylenediamine (OPD).

In certain embodiments a standard sample (e.g., acid-hydrolyzed dextran) can be run under the same conditions to provide a standard set of bands that can be used for alignment purposes.

In certain embodiments, the secondary chromatographic technique is or includes electrochromatography. Electrochromatography is a combination of size exclusion chromatography and gel electrophoresis which is traditionally used to resolve and separate large analytes such as proteins. These separation mechanisms operate essentially in superposition along the length of a gel filtration column to which an axial electric field gradient has been added. The analytes are separated by size due to the gel filtration mechanism and by electrophoretic mobility due to the gel electrophoresis mechanism. Additionally there are secondary chromatographic analyte retention mechanisms.

In certain embodiments, the secondary chromatographic technique is or includes micellar electrokinetic chromatography. Micellar electrokinetic chromatography (MEKC) is a chromatographic technique in which components in a mixture are separated by differential partitioning between a pseudo-stationary micellar phase and an aqueous mobile phase. In most applications, MEKC is performed in open capillaries under alkaline conditions to generate a strong electroosmotic flow. The basic set-up and detection methods used for MEKC are the same as those used in capillary electophoresis that were discussed above. The difference is that the solution contains a surfactant at a concentration that is greater than the critical micelle concentration (CMC). Above this concentration, surfactant monomers are in equilibrium with micelles. Sodium dodecyl sulfate (SDS) is the most commonly used surfactant in MEKC applications. The anionic character of the sulfate groups of SDS cause the surfactant and micelles to have electrophoretic mobility that is counter to the direction of the strong electroosmotic flow. As a result, the surfactant monomers and micelles migrate quite slowly, though their net movement is still toward the cathode. During a MEKC separation, the components of the mixture distribute themselves between the hydrophobic interior of the micelle and hydrophilic buffer solution.

In general, any of these chromatographic techniques may be performed in an HPLC (high performance liquid chromatography) format which is a type of chromatography in which the eluting solvent is conveyed through the column under high pressure (e.g., approximately 200 psi to 6,000 psi). Chromatographic techniques such as anion exchange chromatography (AIEC-HPLC), reversed phase liquid chromatography (RP-HPLC), normal phase liquid chromatography (NP-HPLC), ion-pairing reverse phase chromatography (IPRP-HPLC), and aqueous normal phase chromatography (ANP-HPLC) may all be performed in an HPLC format. It will also be appreciated that in certain embodiments, any one of these chromatographic techniques may be performed in an UPLC (ultra performance liquid chromatography) format in which the eluting solvent is conveyed through a column with very small particle sizes (e.g., between 1.7 microns to 1 micron) under ultra high pressures (e.g., 15,000 psi to 100,000 psi). As can be understood from the above discussion, the present disclosure provides, in part, for the use of a multi-dimensional chromatographic method wherein anion-exchange chromatography is used to perform the initial separation of the glycan preparation (i.e., first dimension) and any of the above-described secondary chromatographic methods can be used to perform subsequent secondary separations (e.g., in the second, third, fourth, fifth dimensions).

For example, in certain embodiments, the method comprises separation of a glycan preparation by anion exchange chromatography (AIEC) followed by either reverse phase or normal phase chromatography.

In certain embodiments, the method comprises separation of a glycan preparation by anion exchange chromatography (AIEC) using a Q resin or DEAE resin followed by either reverse phase or normal phase chromatography.

In certain embodiments, the method comprises separation of a glycan preparation by anion exchange chromatography (AIEC) followed by HPLC chromatography using amide-modified silica gel (normal phase) or PGC (reverse phase). In certain embodiments, the amide-modified silica gel is GlycoSep-N.

In certain embodiments, the method comprises separation of a glycan preparation by anion exchange chromatography (AIEC) followed by reverse phase chromatography using PGC.

In certain embodiments, the method comprises separation of a glycan preparation by anion exchange chromatography (AIEC) followed by reverse phase chromatography, which is further followed by normal phase chromatography.

For example, in certain embodiments, the method comprises separation of a glycan preparation by anion exchange chromatography (AIEC) using a Q resin or DEAE resin followed by reverse phase chromatography using PGC, which is further followed by normal phase chromatography using amide-modified silica gel. In certain embodiments, the amide-modified silica gel is GlycoSep-N.

Applications

It will be appreciated that the techniques described herein can be utilized in any of a variety of applications. In general, these techniques are useful in any application that involves the structural characterization of glycans. Techniques of the present disclosure may be particularly useful in a context that requires the separation of certain glycans in a glycan preparation. It will be appreciated that the techniques can be used with any sample that includes at least one negatively charged N-glycan irrespective of the nature of any additional sample components.

Methods of the present disclosure can be applied to glycan preparations obtained from a wide variety of sources including, but not limited to, therapeutic formulations and biological samples. A biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, glycans in a biological sample are labeled with one or more detectable markers or other agents that may facilitate analysis by, for example, mass spectrometry or NMR. For purposes of illustration, examples of such steps are described in more detail below. Any of a variety of separation and/or isolation steps may be applied to a biological sample in accordance with the present disclosure.

Methods of the present disclosure can be utilized to analyze glycans in any of a variety of states including, for instance, free glycans, glycoconjugates (e.g., glycopeptides, glycolipids, proteoglycans, etc.), or cells or cell components, etc.

Methods of the present disclosure may be used to significantly expedite one or more stages of process development for the production of a therapeutic or other commercially relevant glycoprotein of interest. Non-limiting examples of such process development stages that can be improved using methods of the present disclosure include cell selection, clonal selection, media optimization, culture conditions, process conditions, and/or purification procedure. Those of ordinary skill in the art will be aware of other process development stages that can be improved.

The methods can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The methods can also be utilized to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

In some embodiments of the disclosure, a desired glycosylation pattern for a particular target glycoprotein is known, and the technology described herein allows the monitoring of culture samples to assess progress of the production along a route known to produce the desired glycosylation pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to identical with the established glycosylation pattern of the pharmaceutical product as possible, whether or not it is being produced by exactly the same route. As used herein, "close to identical" refers to a glycosylation pattern having at least 90%, 95%, 98% or 99% correlation to the established glycosylation pattern of the pharmaceutical product. In such embodiments, samples of the production culture are typically taken at multiple time points and are compared with an established standard or with a control culture in order to assess relative glycosylation.

In some embodiments of the present disclosure, a desired glycosylation pattern will be more extensive. For example, in some embodiments, a desired glycosylation pattern shows high (e.g., greater than about 60%, 65%, 70%, 75%, 80%, 85%, 90%, 95% or more) occupancy of glycosylation sites; in some embodiments, a desired glycosylation pattern shows, a high degree of branching (e.g., greater than about 60%, 65%, 70%, 75%, 80%, 85%, 90%, 95% or more have tri or tetraantennary structures).

In some embodiments of the present disclosure, a desired glycosylation pattern will be less extensive. For example, in some embodiments, a desired glycosylation pattern shows low (e.g., less than about 35%, 30%, 25%, 20%, 15% or less) occupancy of glycosylation sites; and/or a low degree of branching (e.g., less than about 20%, 15%, 10%, 5%, or less have tri or tetraantennary structures).

In some embodiments, a desired glycosylation pattern will be more extensive in some aspects and less extensive than others. For example, it may be desirable to employ a cell line that tends to produce glycoproteins with long, unbranched oligosaccharide chains. Alternatively, it may be desirable to employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, 15%, 10%, 5%, or less) of high mannose or hybrid structures, high (e.g., more than about 60%, 65%, 70%, 75%, 80%, 85%, 90% or more) levels of high mannose structures, or high (e.g., more than about 60%, 65%, 70%, 75%, 80%, 85%, 90% or more; for example at least one per glycoprotein) or low (e.g., less than about 20%, 15%, 10%, 5%, or less) levels of phosphorylated high mannose.

In some embodiments, a desired glycosylation pattern will include at least about one sialic acid. In some embodiments, a desired glycosylation pattern will include a high (e.g., greater than about 60%, 65%, 70%, 75%, 80%, 85%, 90%, 95% or more) level of termini that are sialylated. In some embodiments, a desired glycosylation pattern that includes sialylation will show at least about 85%, 90%, 95% or more N-acetylneuraminic acid and/or less than about 15%, 10%, 5% or less N-glycolylneuraminic acid.

In some embodiments, a desired glycosylation pattern shows specificity of branch elongation (e.g., greater than about 50%, 55%, 60%, 65%, 70% or more of extension is on $\alpha 1,6$ mannose branches, or greater than about 50%, 55%, 60%, 65%, 70% or more of extension is on $\alpha 1,3$ mannose branches).

In some embodiments, a desired glycosylation pattern will include a low (e.g., less than about 20%, 15%, 10%, 5%, or less) or high (e.g., more than about 60%, 65%, 70%, 75%, 80%, 85%, 90%, 95%, or more) level of core fucosylation.

Whether or not monitoring production of a particular target protein for quality control purposes, the present disclosure may be utilized, for example, to monitor glycosylation at particular stages of development, or under particular growth conditions.

In some particular embodiments of the present disclosure, the methods can be used to characterize and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the methods can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for instance, erythropoietins, blood-clotting factors, etc.), interferons, colony stimulating factors, antibodies, enzymes, and hormones.

Representative commercially available glycoprotein products include, for example:

| Protein Product | Reference Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AiphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamiein | Mylotarg ™ |
| galsulfase | Naglazyme ™ |
| nesiritide | Natrecor ® |
| pegfilgrastim | Neulasta ™ |
| oprelvekin | Neumega ® |

-continued

| Protein Product | Reference Drug |
|---|---|
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

In some embodiments, the disclosure provides methods in which glycans from different sources or samples are compared with one another. In certain embodiments, the disclosure provides methods used to monitor the extent and/or type of glycosylation occurring in different cell cultures. In some such examples, multiple samples from the same source are obtained over time, so that changes in glycosylation patterns (and particularly in cell surface glycosylation patterns) are monitored. In some embodiments, one of the samples is a historical sample or a record of a historical sample. In some embodiments, one of the samples is a reference sample. For example, in certain embodiments, methods are provided herein which can be used to monitor the extent and/or type of glycosylation occurring in different cell cultures.

In some embodiments, glycans from different cell culture samples prepared under conditions that differ in one or more selected parameters (e.g., cell type, culture type [e.g., continuous feed versus batch feed, etc.], culture conditions [e.g., type of media, presence or concentration of particular component of particular medium, osmolarity, pH, temperature, timing or degree of shift in one or more components such as osmolarity, pH, temperature, etc.], culture time isolation steps, etc.) but are otherwise identical, are compared, so that effects of the selected parameter(s) on N-glycosylation patterns are determined. In certain embodiments, glycans from different cell culture samples prepared under conditions that differ in a single selected parameter are compared so that effect of the single selected parameter on the glycosylation pattern is determined. Among other applications, therefore, use of techniques as described herein may facilitate determination of the effects of particular parameters on glycosylation patterns in cells.

In some embodiments, glycans from different batches of a glycoprotein of interest (e.g., a therapeutic glycoprotein), whether prepared by the same method or by different methods, and whether prepared simultaneously or separately, are compared. In such embodiments, the methods facilitate quality control of glycoprotein preparation. Alternatively or additionally, some such embodiments facilitate monitoring of progress of a particular culture producing a glycoconjugate of interest (e.g., when samples are removed from the culture at different time points and are analyzed and compared to one another). In any of these embodiments, features of the glycan analysis can be recorded, for example in a quality control record. As indicated above, in some embodiments, a comparison is with a historical record of a prior or standard batch and/or with a reference sample of glycoprotein.

In certain embodiments, the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, techniques of the present disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids).

In some particular embodiments, cell surface glycans are analyzed in order to assess glycosylation of one or more target glycoproteins of interest, particularly where such target glycoproteins are not cell surface glycoproteins. Such embodiments can allow one to monitor glycosylation of a target glycoprotein without isolating the glycoprotein itself. In certain embodiments, the present disclosure provides methods of using cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods of the present disclosure can avoid the effort required for isolation of product and the potential selection of product glycoforms that may occur during isolation.

In certain embodiments, techniques of the present disclosure are applied to glycans that are secreted from cells. In some such embodiments, the analyzed glycans are produced by cells in the context of a glycoconjugate (e.g., a glycoprotein or glycolipid).

Techniques described herein can be used to detect desirable or undesirable glycans, for example to detect or quantify the presence of one or more contaminants in a product, or to detect or quantify the presence of one or more active or desired species.

In various embodiments the methods can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, the methods facilitate detection of glycans that are present at very low levels in a source (e.g., a biological sample). In such embodiments, it is possible to separate over 10, 20, 30, 40, 50, 60, 70, 80, 90 or 100 glycan components of a mixture, and to detect and optionally quantify the levels of glycans comprising between 0.1% and 5%, e.g., between 0.1% and 2%, e.g., between 0.1% and 1% of the original glycan preparation. In certain embodiments, it is possible to detect and/or optionally quantify the levels of glycans at between about 0.1 fmol to about 1 mmol.

In some embodiments, the techniques may be combined with one or more other technologies for the detection, analysis, and or isolation of glycans or glycoconjugates.

Thus, in certain embodiments, the methods comprise releasing N-linked glycans from a glycoconjugate or cell surface to provide a glycan preparation that includes a mixture of N-glycans. In certain embodiments, the mixture of N-glycans is provided via cleavage of N-linked glycans from a glycoprotein after the cell surface glycoproteins have been liberated from the cell (e.g., through treatment with one or more proteases and/or glycosidases). In certain embodiments, the mixture of N-glycans is provided via cleavage of N-linked glycans from cell surface glycoproteins that have not been liberated from the cell. N-linked glycans may be released (e.g., separated, cleaved, hydrolyzed) using a variety of chemical or enzymatic methods; see generally, Kamerling, *Pure Appl. Chem.* (1994) 66:2235-2238; Kamerling and Vliegnenthart, in: *Clinical Biochemistry, Principles, Methods, Applications*, Volume 1 (A. N. Lawson, ed), Walter De Gruyter, Berlin (1989) pp. 175-263; and Allen and Kisailus, eds., *Glycoconguates*, Marcel Dekker Inc., New York, 1992.

Thus, in one aspect, a multi-dimensional chromatographic method for the separation of a glycan preparation is provided which comprises the steps of:

(i) cleaving N-linked glycans from a glycoprotein preparation to provide a glycan preparation that includes a mixture of N-glycans, wherein at least one of the N-glycans in the glycan preparation is negatively charged; and (ii) separating the glycan preparation by anion-exchange chromatography and at least one secondary chromatographic technique.

Any of a variety of glycosidases that cleave glycan structures from glycoproteins, or cell surface glycoproteins, may be used in accordance with the present disclosure. Several examples of such glycosidases are reviewed in R. A. O'Neill, *Enzymatic release of oligosaccharides from glycoproteins for chromatographic and electrophoretic analysis*, J. Chromatogr. A 720, 201-215. 1996; and S. Prime, et al., *Oligosaccharide sequencing based on exo- and endo-glycosidase digestion and liquid chromatographic analysis of the products*, J. Chromatogr. A 720, 263-274, 1996. In certain embodiments, the enzyme PNGase F (Peptide N-Glycosidase F) is used to remove glycans from a glycoprotein. PNGase F is an amidase that cleaves the amide bond between the innermost GlcNAc and asparagine residues of high mannose, hybrid, and complex oligosaccharides from N-linked glycoproteins. Other suitable enzymes that can be used to cleave glycan structures from glycoproteins in accordance with the present disclosure include, but are not limited to, PNGase A and endoglycosidases (Endo-H). Those of ordinary skill in the art will be aware of other suitable enzymes for cleavage of glycans from glycoproteins. In certain embodiments, a plurality of enzymes is used to cleave glycan structures from a glycoprotein.

To improve the accessibility of the glycosylation site to the enzyme, most glycoproteins require a protein denaturation step. Typically, this is accomplished by using detergents and disulfide-reducing agents, although methods of denaturing a glycoprotein for use in accordance with the present disclosure are not limited to the use of such agents. For example, exposure to high temperature can be sufficient to denature a glycoprotein such that a suitable enzyme for cleaving glycan structures is able to access the cleavage site. In certain embodiments, a combination of detergents, disulfide-reducing agents, high temperature, and/or other agents or reaction conditions is employed to denature a glycoprotein. It is noted that glycans located at conserved Fc sites in immunoglobulin G (IgG) are easily cleaved by PNGase F. Thus, a protein denaturation step is typically not required for IgG molecules. PNGase F is also capable of removing glycans in dilute ammonium hydroxide solution. Thus, use of PNGase F to cleave glycans from glycoproteins has the advantage that the dilute ammonium hydroxide may additionally aid in solubility and some unfolding of the protein substrates.

Additionally, N-linked glycans may be cleaved from a glycoprotein using chemical methods. For example, an N-linked glycan may be released via treatment with hydrazine to provide a hydrazide of the N-glycan (i.e., hydrazinolysis).

Additionally, following cleavage of the N-linked glycan from the glycoprotein or cell-surface glycoprotein, the N-glycans may be purified to remove non-carbohydrate contaminants, such as salts, chemicals, and detergents used in enzymatic digests. The methods of purification may include, but are not limited to, the use of C18 and graphitized carbon cartridges and spin columns. In other embodiments, the method of purification may include a step of acetone precipitation of proteinaceous material from an ice-cold aqueous solution containing both proteins and glycans.

In certain embodiments, prior to separation according to the present disclosure, some or all of the N-glycans in the glycan preparation may be derivatized with a label agent (e.g., a fluorescent or UV-active label). This label enables a higher sensitivity of detection of the glycan during chromatographic separation. Labeling agents for this purpose are described in the art, e.g., see Anumula, *Anal. Biochem.* (2006) 350:1-23; Lamari et al., *J. Chromatogr. B* (2003) 793:15-36; Bigge et al., *Anal. Biochem.* (1995) 230:229-238, and references provided therein.

Thus, in certain embodiments, a multi-dimensional chromatographic method for the separation of a mixture of N-glycans is provided which comprises the steps of:

(i) cleaving N-linked glycans from a glycoprotein preparation to provide a glycan preparation that includes a mixture of N-glycans, wherein at least one of the N-glycans in the glycan preparation is negatively charged; and (ii) reacting the glycan preparation with a labeling agent to provide a glycan preparation that includes a mixture of labeled N-glycans; and then (iii) separating the glycan preparation by anion-exchange chromatography and at least one secondary chromatographic technique.

Exemplary fluorescent labeling agents include, but are not limited to, 2-d aminobenzoic acid (2AA); 3-aminobenzoic acid (3AA); 4-aminobenzoic acid (4AA); anthranilic acid (AA); 2-aminopyridine (2AP); 2-aminobenzamide (2AB); 3-aminobenzamide (3AB); 4-aminobenzamide (4AB); 2-aminobenzoic ethyl etser (2ABEE); 3-aminobenzoic ethyl etser (3ABEE); 4-aminobenzoic ethyl etser (4ABEE); 2-aminobenzonitrile (2ABN); 3-aminobenzonitrile (3ABN); 4-aminobenzonitrile (4ABN); 3-(acetylamino)-6-aminoacridin (AA-AC); 2-aminoacridone (AMAC); methylanthranilate (MA); 6-aminoquinoline (6AQ); 8-aminonaphthalene-1,3,6-trisulfonic acid (ANTS); 2-aminonaphthalene-1,3,6-trisulfonate (ANT); 8-aminopyrene-1,3,6-trisulfonic acid (APTS); 7-aminomethyl-coumarin (AMC); 2-amino(6-amido-biotinyl)pyridine (BAP); 9-fluorenylmethoxy-carbonyl-hydrazide (FMOC-hydrazide); 3,5-dimethylanthranilic acid, and 2-amino-4,5-dimethoxy-benzoic acid.

The present disclosure contemplates use of any and all known "labeling agents" for labeling of N-glycans, as provided above and herein.

Additionally, the present disclosure contemplates use of any and all "labeling agents" for labeling of N-glycans, encompassed by the formulae (I) and (II), as depicted below,

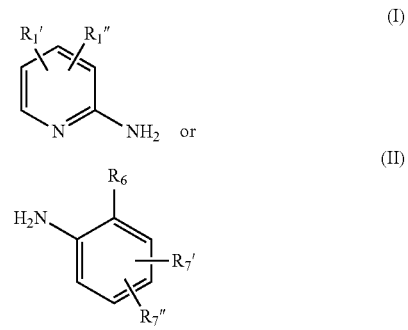

wherein $R_1'$ and $R_1''$ are each independently —H, —$NH_2$, —$NHR_2$, —$CONH_2$, —COOH, —$COR_3$, —$COOR_4$, —$SO_3$, —$SO_nR_5$ where n is 1 or 2, or a substituted or unsubstituted, cyclic or acyclic, branched or unbranched alkyl, substituted or unsubstituted, cyclic or acyclic, branched or unbranched alkenyl, substituted or unsubstituted, cyclic or acyclic, branched or unbranched alkynyl, substituted or unsubstituted, cyclic or acyclic, branched or unbranched heteroalkyl, substituted or unsubstituted aryl or substituted or unsubstituted heteroaryl group, or when attached to adjacent carbon atoms $R_1'$ and $R_1''$ may be taken together with the atoms to which they are attached to form a 5- to 7-membered ring optionally containing a heteroatom selected from O, N or S;

$R_2$, $R_3$, $R_4$ and $R_5$ are each independently —H or substituted or unsubstituted, cyclic or acyclic, branched or unbranched alkyl, substituted or unsubstituted, cyclic or acyclic, branched or unbranched alkenyl, substituted or unsubstituted, cyclic or acyclic, branched or unbranched alkynyl, substituted or unsubstituted, cyclic or acyclic, branched or unbranched heteroalkyl, substituted or unsubstituted aryl or substituted or unsubstituted heteroaryl group;

$R_6$ is —H, $NH_2$, —$NHR_2$, —$CONH_2$, —COOH, —$COR_3$, —$COOR_4$, —$SO_3$ or —SO—$R_5$ where n is 1 or 2;

$R_7'$ and $R_7''$ are each independently —H, —$NH_2$, —$NHR_2$, —$CONH_2$, —COOH, —$COR_3$, —$COOR_4$, —$SO_3$, —$SO_nR_5$ where n is 1 or 2, or an substituted or unsubstituted, cyclic or acyclic, branched or unbranched alkyl, substituted or unsubstituted, cyclic or acyclic, branched or unbranched alkenyl, substituted or unsubstituted, cyclic or acyclic, branched or unbranched alkynyl, substituted or unsubstituted, cyclic or acyclic, branched or unbranched heteroalkyl, substituted or unsubstituted aryl or substituted or unsubstituted heteroaryl group, or when attached to adjacent carbon atoms $R_1$ and $R_1'$ may be taken together with the atoms to which they are attached to form a 5- to 7-membered ring optionally containing a heteroatom selected from O, N or S, and wherein any one of the hydrogen atoms is optionally isotopically labeled as $^2$H or $^3$H; any one of the carbon atoms is optionally isotopically labeled as $^{13}$C; any one of the oxygen atoms is optionally isotopically labeled as $^{18}$O; any one of the nitrogen atoms is optionally isotopically labeled as $^{15}$N; and any one of the sulfur atoms is optionally isotopically labeled as $^{33}$S or $^{34}$S.

In certain embodiments, $R_1'$ and $R_1''$ are each independently —H, —NH$_2$, —NHR$_2$, —CONH$_2$, —COOH, —COR$_3$, —COOR$_4$, —SO$_3$, —SO$_n$R$_5$ where n is 1 or 2, or unsubstituted, cyclic or acyclic alkyl; unsubstituted, cyclic or acyclic alkenyl; unsubstituted, cyclic or acyclic alkynyl; unsubstituted, cyclic or acyclic heteroalkyl; unsubstituted aryl, or unsubstituted heteroaryl group, or when attached to adjacent carbon atoms $R_1'$ and $R_1''$ may be taken together with the atoms to which they are attached to form a 5- to 7-membered ring optionally containing a heteroatom selected from O, N or S.

In certain embodiments, $R_2$, $R_3$, $R_4$ and $R_5$ are each independently H or unsubstituted, cyclic or acyclic alkyl; unsubstituted, cyclic or acyclic alkenyl; unsubstituted, cyclic or acyclic alkynyl; unsubstituted, cyclic or acyclic heteroalkyl, unsubstituted aryl or unsubstituted heteroaryl group.

In certain embodiments, $R_7'$ and $R_7''$ are each, independently, —H, —NH$_2$, —NHR$_2$, —CONH$_2$, —COOH, —COOR$_4$, —SO$_3$, —SO$_n$R$_5$ where n is 1 or 2, or unsubstituted, cyclic or acyclic alkyl, unsubstituted, cyclic or acyclic alkenyl, unsubstituted, cyclic or acyclic alkynyl, unsubstituted, cyclic or acyclic heteroalkyl, unsubstituted aryl or unsubstituted heteroaryl group, or when attached to adjacent carbon atoms $R_1$ and $R_1'$ may be taken together with the atoms to which they are attached to form a 5- to 7-membered ring optionally containing a heteroatom selected from O, N or S.

The above labeling agents are used to label the glycan via reaction of the amine function group of the labeling agent with the N-glycan's reducing (—CHO) end by reductive amination (see Scheme 1). One of ordinary skill in the art will appreciate that a wide variety of reaction conditions may be employed to promote this reductive amination reaction, therefore, a wide variety of reaction conditions are envisioned; see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999. Suitable reductive amination conditions include providing a reducing agent, such as NaCNBH$_3$ or NaBH(OAc)$_3$, and maintaining an acidic to slightly acidic pH of the reaction mixture.

Scheme 1.

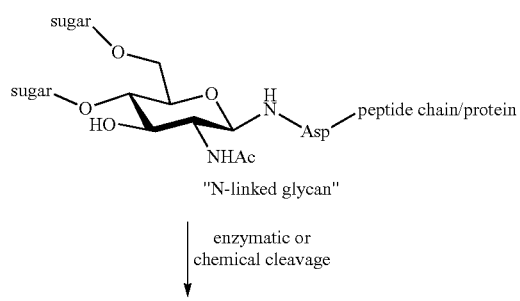

Labeling of the N-glycan is not limited to derivatization of the reducing end. The present disclosure also provides suitable labeling agents for tagging other functional groups present on the glycan moiety. For example, as depicted in Scheme 2, 1,2-diamino functionalized labeling agents, such as 1,2-diamino-4,5-methylenedioxy-benzene (DMB) and ortho-phenylenediamine (OPD), are suitable for tagging via reaction with the alpha-keto acid functional group of sialic acids.

Furthermore, after labeling and separation steps according to the methods described herein, the isolated labeled N-glycans may be purified to remove non-carbohydrate contaminants, such as salts, excess chemicals, and acids, used during the labeling reaction.

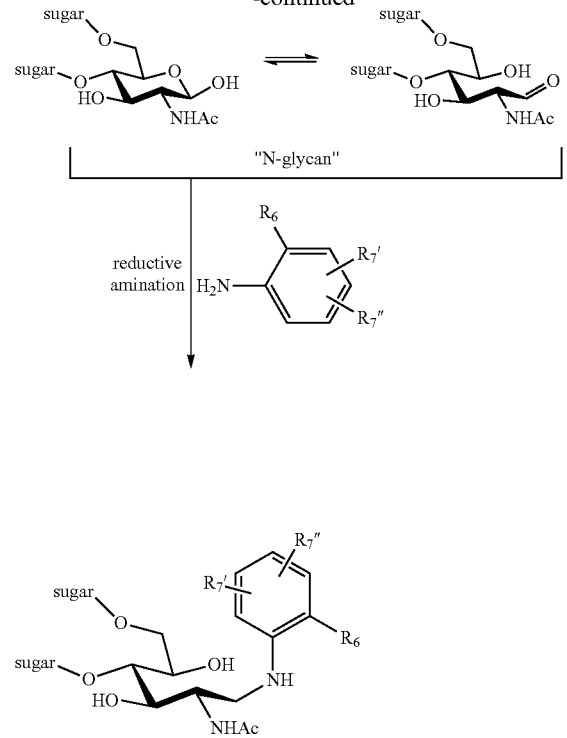

Scheme 2.

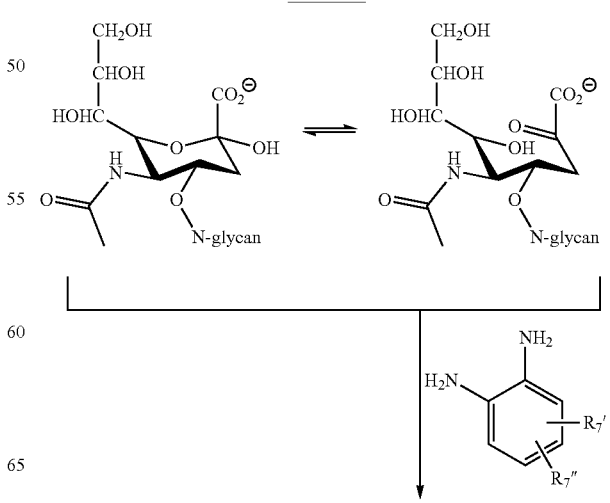

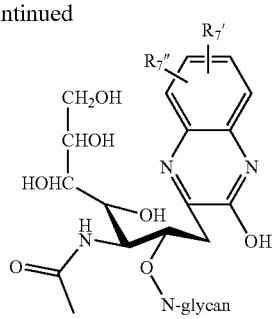

Definitions of specific functional groups and chemical terms are described in more detail below. For purposes of this disclosure, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

In general, the term "substituted" refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein and any combination thereof that results in the formation of a stable moiety. The present disclosure contemplates any and all such combinations in order to arrive at a stable substituent/moiety. For purposes of this disclosure, heteroatoms such as nitrogen may have hydrogen substituents and/or any suitable substituent as described herein which satisfy the valencies of the heteroatoms and results in the formation of a stable moiety. The term "stable moiety," as used herein, preferably refers to a moiety which possess stability sufficient to allow manufacture, and which maintains its integrity for a sufficient period of time to be useful for the purposes detailed herein.

The term "alkyl," as used herein, refers to saturated, cyclic or acyclic, branched or unbranched, substituted or unsubstituted hydrocarbon radicals derived from a hydrocarbon moiety containing between one and twenty carbon atoms by removal of a single hydrogen atom. In some embodiments, the alkyl group contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, alkyloxy, aryloxy, alkyloxyalkyl, azido, oxo, cyano, halo, isocyano, nitro, nitroso, azo, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; haloalkyl, alkoxyalkyl, substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "cycloalkyl" refers to a cyclic alkyl group, as defined herein. Cycloalkyl groups include cyclopropyl, cyclobutyl, cyclopentyl, cyclhexyl, cycloheptyl, cyclooctyl, cyclononyl, cyclodecyl, cycloundecyl, cyclododecyl, and the like, which may bear one or more substitutents. Cycloalkyl group substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, alkyloxy, aryloxy, alkyloxyalkyl, azido, cyano, halo, isocyano, nitro, nitroso, azo, oxo, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "alkenyl," as used herein, denotes a monovalent group derived from a cyclic or acyclic, branched or unbranched, substituted or unsubstituted hydrocarbon moiety having at least one carbon-carbon double bond by the removal of a single hydrogen atom. In certain embodiments, the alkenyl group contains 2-20 carbon atoms. In some embodiments, the alkenyl group contains 2-15 carbon atoms. In another embodiment, the alkenyl group employed contains 2-10 carbon atoms. In still other embodiments, the alkenyl group contains 2-8 carbon atoms. In yet another embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, haloalkyl, alkyloxy, aryloxy, alkyloxyalkyl, azido, cyano, halo, isocyano, nitro, nitroso, azo, oxo, —$CONH_2$, —COOH, —$COR_3$, —$COOR_4$, —$SO_3$, —$SO_nR_5$, wherein n is 1 or 2, and $R_2$, $R_3$, $R_4$ and $R_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "alkynyl," as used herein, refers to a monovalent group derived from a cyclic or acyclic, branched or unbranched, substituted or unsubstituted hydrocarbon having at least one carbon-carbon triple bond by the removal of a single hydrogen atom. In certain embodiments, the alkynyl group contains 2-20 carbon atoms. In some embodiments, the alkynyl group contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, alkyloxy, aryloxy, alkyloxyalkyl, azido, cyano, halo, isocyano, nitro, nitroso, azo, oxo, —$CONH_2$, —COOH, —$COR_3$, —$COOR_4$, —$SO_3$, —$SO_nR_5$, wherein n is 1 or 2, and $R_2$, $R_3$, $R_4$ and $R_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "heteroalkyl," as used herein, refers to an alkyl moiety, as defined herein, which includes saturated, cyclic or acyclic, branched or unbranched, substituted or unsubstituted hydrocarbon radicals, which contain one or more oxygen, sulfur, nitrogen, phosphorus, or silicon atoms, e.g., in place of carbon atoms. In certain embodiments, heteroalkyl moieties are substituted by independent replacement of one or more of the hydrogen atoms thereon with one or more substituents. Heteroalkyl substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, alkyloxy, aryloxy, alkyloxyalkyl, azido, cyano, halo, isocyano, nitro, nitroso, azo, oxo, —$CONH_2$, —COOH, —$COR_3$, —$COOR_4$, —$SO_3$, —$SO_nR_5$, wherein n is 1 or 2, and $R_2$, $R_3$, $R_4$ and $R_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like. Similarly, the term haloalkoxy designates an $OC_nH_{2n+1}$ group having from one to 2n+1 halogen atoms which may be the same or different.

The term "alkoxyalkyl", as used herein, refers to an alkyl group as hereinbefore defined substituted with at least one alkyloxy group.

The term "cycloheteroalkyl," as used herein, refers to a cyclic heteroalkyl group as defined herein. A cycloheteroalkyl group refers to a fully saturated 3- to 10-membered ring system, which includes single rings of 3 to 8 atoms in size. These cycloheteroalkyl rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term cycloheteroalkyl refers to a 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Examples of cycloheteroalkyl ring systems included in the term as designated herein are the following rings wherein $X_1$ is NR', O or S, and R' is H or an optional substituent as defined herein:

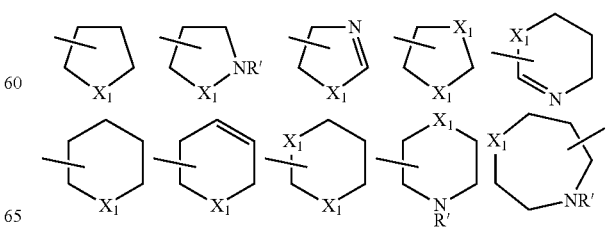

Exemplary cycloheteroalkyls include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, alkyloxy, aryloxy, alkyloxyalkyl, azido, cyano, halo, isocyano, nitro, nitroso, azo, oxo, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group)

The term "aryl," as used herein, refer to stable aromatic mono- or polycyclic ring system having 3-20 ring atoms, of which all the ring atoms are carbon, and which may be substituted or unsubstituted. In certain embodiments of the present disclosure, "aryl" refers to a mono, bi, or tricyclic C$_4$-C$_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, alkyloxy, aryloxy, alkyloxyalkyl, azido, cyano, halo, isocyano, nitro, nitroso, azo, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, substituted or unsubstituted thio, haloalkyl, alkyloxy, aryloxy, alkyloxyalkyl, azido, cyano, halo, isocyano, nitro, nitroso, azo, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group)

The term "amino," as used herein, refers to a group of the formula (—NH$_2$). A "substituted amino" refers either to a mono-substituted amine (—NHR$^h$) or a di-substituted amine (—NR$^h_2$), wherein the R$^h$ substituent is any substitutent as described herein that results in the formation of a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, substituted or unsubstituted amino, substituted or unsubstituted hydroxy, haloalkyl, alkyloxy, aryloxy, alkyloxyalkyl, azido, cyano, halo, oxo, —CONH$_2$, —COOH, —COR$_3$, —COOR$_4$, —SO$_3$, —SO$_n$R$_5$ wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group). In certain embodiments, the R$^h$ substituents of the di-substituted amino group (—NR$^h_2$) form a 5- to 6-membered cycloheteroalkyl ring.

The term "hydroxy," or "hydroxyl," as used herein, refers to a group of the formula (—OH). A "substituted hydroxyl" refers to a group of the formula (—OR$^i$), wherein R$^i$ can be any substituent which results in a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "thio" or "thiol" as used herein, refers to a group of the formula (—SH). A "substituted thiol" refers to a group of the formula (—SR$^r$), wherein R$^r$ can be any substituent which results in a stable moiety (e.g., cyclic or acyclic, branched or unbranched, substituted or unsubstituted alkyl, cyclic or acyclic, branched or unbranched, substituted or unsubstituted alkenyl, cyclic or acyclic, branched or unbranched, substituted or unsubstituted alkynyl, substituted or unsubstituted aryl, substituted or unsubstituted heteroaryl, —CONH$_2$, —COOH, —COR$_3$, —COOR$_4$, —SO$_3$, —SO$_n$R$_5$, wherein n is 1 or 2, and R$_2$, R$_3$, R$_4$ and R$_5$ are each independently —H or substituted or unsubstituted, cyclic or acyclic, branched or unbranched alkyl; substituted or unsubstituted, cyclic or acyclic, branched or unbranched alkoxyalkyl; substituted or unsubstituted, cyclic or acyclic, branched or unbranched alkenyl; substituted or unsubstituted, cyclic or acyclic, branched or unbranched alkynyl; substituted or unsubstituted, cyclic or acyclic, branched or unbranched cycloalkyl, substituted or unsubstituted, cyclic or acyclic, branched or unbranched cycloheteroalkyl, substituted or unsubstituted aryl or substituted or unsubstituted heteroaryl group).

The term "alkyloxy" refers to a "substituted hydroxyl" of the formula (—OR$^i$), wherein R$^i$ is an optionally substituted alkyl group, as defined herein, and the oxygen moiety is directly attached to the parent molecule. The term "alkylthioxy" refers to a "substituted thiol" of the formula (—SR$^r$), wherein R$^r$ is an optionally substituted alkyl group, as defined herein, and the sulfur moiety is directly attached to the parent molecule. The term "alkylamino" refers to a "substituted amino" of the formula (—NR$^h{}_2$), wherein R$^h$ is, independently, a hydrogen or an optionally substituted alkyl group, as defined herein, and the nitrogen moiety is directly attached to the parent molecule.

The term "aryloxy" refers to a "substituted hydroxyl" of the formula (—OR$^i$), wherein R$^i$ is an optionally substituted aryl group, as defined herein, and the oxygen moiety is directly attached to the parent molecule. The term "arylamino," refers to a "substituted amino" of the formula (—NR$^h{}_2$), wherein R$^h$ is, independently, a hydrogen or an optionally substituted aryl group, as defined herein, and the nitrogen moiety is directly attached to the parent molecule. The term "arylthioxy" refers to a "substituted thiol" of the formula (—SR$^r$), wherein R$^r$ is an optionally substituted aryl group, as defined herein, and the sulfur moiety is directly attached to the parent molecule.

The term "alkyloxyalkyl" or "alkoxyalkyl" as used herein refers to an alkyloxy group, as defined herein, attached to an alkyl group attached to the parent molecule.

The term "azido," as used herein, refers to a group of the formula (—N$_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "isocyano," as used herein, refers to a group of the formula (—NC).

The term "nitro," as used herein, refers to a group of the formula (—NO$_2$).

The term "nitroso," as used herein, refers to a group of the formula (—N=O).

The term "azo," as used herein, refers to a group of the formula (—N$_2$).

The term "oxo," as used herein, refers to a group of the formula (=O).

In some embodiments, the techniques may be combined with one or more other technologies for the detection, analysis, and or isolation of glycans or glycoconjugates. It will be appreciated that once the N-glycans have been separated according to the methods described herein they may be further analyzed by any technique. For example, the N-glycans may be analyzed by mass spectrometry or nuclear magnetic resonance (e.g., using TOCSY, NOESY or HSQC type experiments, etc. to determine structural features). Mass spectroscopic analysis can be performed using methods such as ESI-MS, ESI-MS/MS, MALDI-TOF-MS, MALDI-TOF/TOF-MS, tandem MS, etc.

The methods will be more specifically illustrated with reference to the following examples. However, it should be understood that the methods are not limited by these examples in any manner.

EXAMPLES

Example 1

N-glycans contain different number of sialic acids. In one experiment, we therefore chose to perform the first dimensional separation based on the number of charges of the glycans using anion-exchange chromatography (AIEC). After AIEC, each individual fraction was further separated, using an secondary chromatographic technique. In this particular example we used (a) reverse-phase chromatography to further separate the AIEC glycan fraction corresponding to neutral glycans and/or (b) normal-phase amide chromatography to further separate the AIEC glycan fractions corresponding to acidic, negatively-charged glycans. In addition, the N-glycans were labeled with the fluorescent label 2-AB in order to facilitate the sensitive and quantitative detection of the N-glycans during the separation process.

AIEC separation of an N-glycan pool was performed on a DEAE column (TSK-gel, 7.5 mm×7.5 cm, Tosoh Inc.) using the following conditions:

Column temperature: 40° C.

Buffer A: 10% acetonitrile, 90% H$_2$O; pH 7.

Buffer B: 50% 500 mM ammonium acetate, 40% H$_2$O, 10% acetonitrile; pH 7.

Gradient between Buffer A and Buffer B:

| Time (min) | Flow (ml/min) | % A | % B |
|---|---|---|---|
| 0 | 0.5 | 100 | 0 |
| 5 | 0.5 | 100 | 0 |
| 95 | 0.5 | 40 | 60 |
| 100 | 0.5 | 40 | 60 |
| 101 | 0.5 | 0 | 100 |
| 106 | 0.5 | 0 | 100 |
| 107 | 0.5 | 100 | 0 |
| 120 | 0.5 | 100 | 0 |
| 121 | 0 | 100 | 0 |

FIG. 1 is a representative chromatogram of the AIEC separation using these conditions. The data indicate that the 2-AB labeled N-glycans were separated into several groups based on the number of charges they carried.

After the first dimension of separation, fractions from AIEC were collected offline and concentrated before being subjected to secondary chromatographic separations. Several fractions of 2AB-labeled glycans were collected from the AIEC separation. Each fraction was lyophilized and reconstituted into an appropriate volume for offline injection onto a second secondary dimension of separation.

In one embodiment, the first fraction is further separated in a second dimension by reverse-phase C18 HPLC separation. Separated peaks on this C18 HPLC may be analyzed by offline MALDI MS or by online LC-MS.

In another embodiment, the first fraction is subjected to a second dimension of separation using a normal-phase amide HPLC column. Separated peaks on this amide HPLC may be analyzed by offline MALDI MS or by online LC-MS. For example, the results of separating all of the AIEC fractions on a normal-phase amide HPLC column using an ammonium formate buffer gradient of 0 to 50 mM ammonium formate are shown in FIG. 4. In another embodiment, the later-eluting AIEC glycans (e.g., some or all of fractions 7-11) are subjected to a second offline dimension of separation using a graphitized carbon column HPLC method, instead of a normal-phase HPLC method (e.g., see Example 2). In another embodiment, some or all of the AIEC fractions are analyzed by a second dimension of normal-phase amide chromatography, and then by a third dimension of chromatography, such as (but not limited to) graphitized carbon column chromatography (e.g., see Example 2). In this embodiment, the glycan structures may be analyzed by offline MALDI-MS or by online LC-MS.

Example 2

An N-glycan pool was obtained from a test glycoprotein, and the glycans were fluorescently labeled. They were then fractionated via anion-exchange chromatography, generating fractions "IEX fraction 1, 2, 3", etc. As described below, 10 of these fractions were then further separated by either amide chromatography or PGC (porous graphitized carbon) chromatography. Without limitation, suitable amide columns include the GlycoSep-N, Ludgersep-N1, or Tsk-gel amide-80 columns while other suitable PGC columns include the Supelco envicarb and Thermo Hypercarb columns.

Figure 5G:
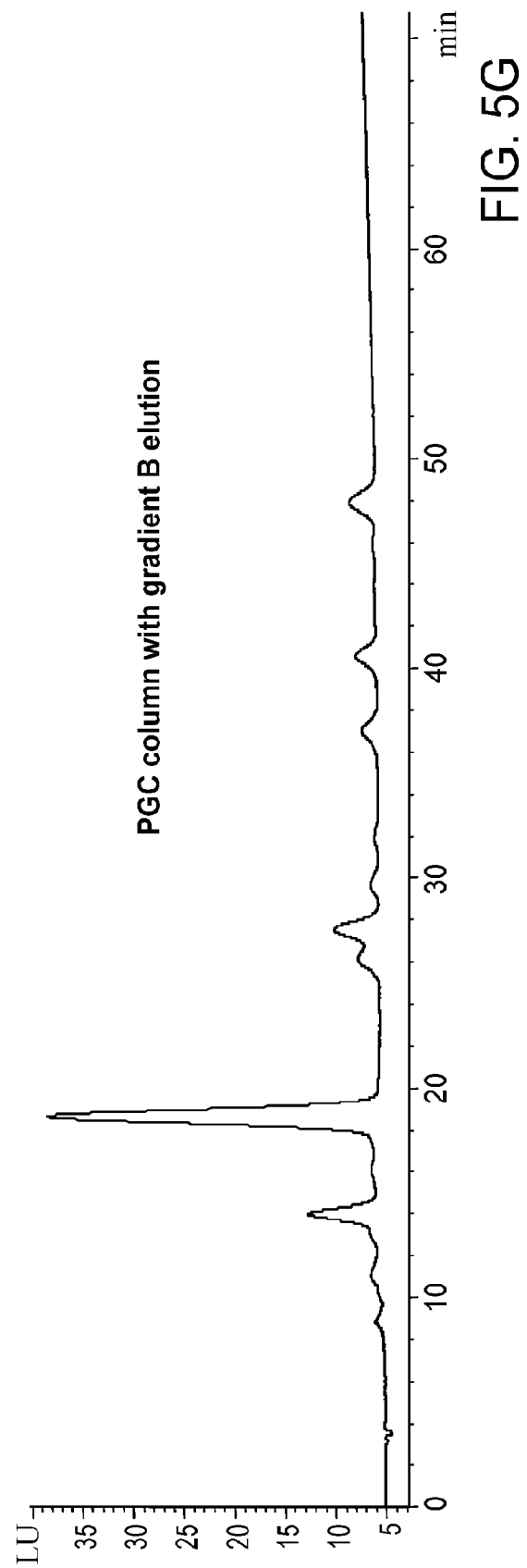

In this experiment, certain fractions obtained from anion exchange chromatography (AIEX or IEX) were separated using an amide column in the second dimension (see FIGS. 5A-E and 6), while other fractions were separated using a PGC column in the second dimension (see FIGS. 5F-G and 7). The areas of resolved peaks can be used to quantify the glycan species. Relative quantities can be obtained using peak ratios. By spiking samples with a known amount of a fluorescently-labeled N,N'-diacetyl chitobiose standard absolute quantitation can be achieved.

A comparison of the panels within FIG. 4 (see Example 1) shows that the later IEX fractions 7-9 and 11 (see FIGS. 4F-J) are in general less well separated on an amide column, than are the earlier IEX fractions 1-6 and 10 (See FIGS. 4A-E, I). We observed a significant improvement in the separation for fraction 7 using the PGC method for the second dimension of separation (compare FIG. 5E and FIGS. 5F-G). Similar results were obtained with fraction 8 (see below) and fraction 9 (data not shown).

The following are typical separation conditions that could be used for an amide column such as the GlycoSep-N column (4.6×250 mm, Prozyme) used in this example:

Column Temperature: 15-50° C.
Buffer A: acetonitrile (50-100%).
Buffer B: 5-250 mM ammonium acetate (or formate or carbonate), pH 4-8.

For example, the separations in FIGS. 5A and 5C were obtained using a GlycoSep-N column (4.6×250 mm, Prozyme) at 45° C., the following binary solvent system (Buffer A: acetonitrile and Buffer B: 50 mM ammonium acetate, pH 7), a 0.75 ml/min flow rate and the following elution gradient:

| Time (mins) | % Buffer B |
|---|---|
| 5 | 35 |
| 77 | 53 |
| 78 | 100 |
| 93 | 100 |
| 94 | 35 |
| 110 | 35 |

The separations in FIGS. 5B and 5D were obtained using the same column system but a shallower 30-48% elution gradient. By tuning the gradient we obtained better separation of fractions 3 and 5, than the steeper 35-53% gradient described in the previous table.

The following are typical separation conditions that could be used for a PGC column such as the Hypercarb column (4.6×150 mm, Thermo) used in this example:

Column Temperature: 15-40° C.
Buffer A: 2-100 mM ammonium acetate (or formate or carbonate), pH 4.5-8.5.
Buffer B: 2-100 mM ammonium acetate (or formate or carbonate), pH 4.5-8.5 in 20-60% acetonitrile.

For example, the separations in FIGS. 5F and 5G were obtained using a Hypercarb column (4.6×150 mm, Thermo) at 30° C., the following binary solvent system (Buffer A: 50 mM ammonium acetate, pH 7 and Buffer B: 50:50 mixture of acetonitrile and 50 mM ammonium acetate, pH 7), a 0.6 ml/min flow rate and the following elution gradient:

| Time (mins) | % Buffer B FIG. 5F | Time (mins) | % Buffer B FIG. 5G |
|---|---|---|---|
| 5 | 42 | 5 | 47 |
| 50 | 80 | 45 | 52 |
| 65 | 80 | 70 | 58 |
| 66 | 42 | 71 | 80 |
| 80 | 42 | 80 | 80 |

Figure 7A:
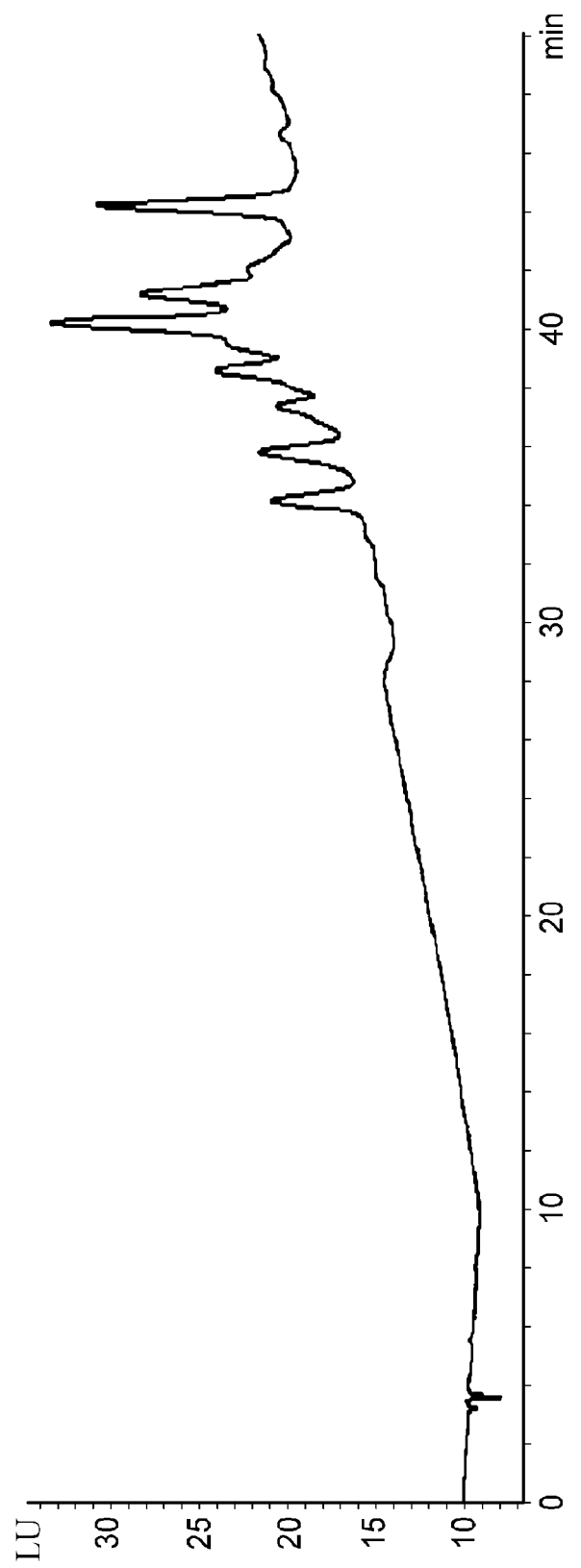
FIG. 7A-7C. Chromatographic resolution of glycans by a second dimensional PGC column method.
Figure 7B:
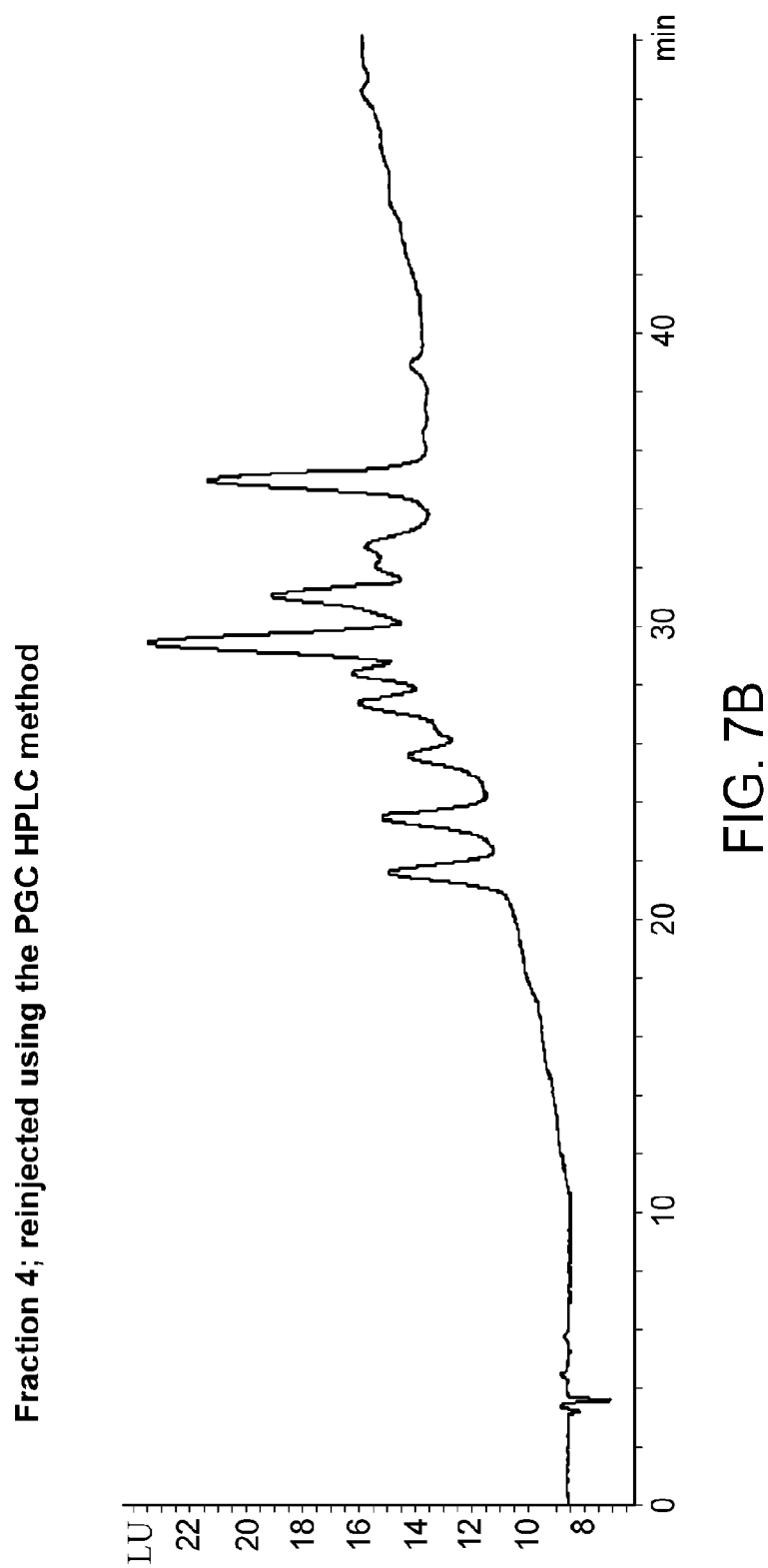
Figure 7C:
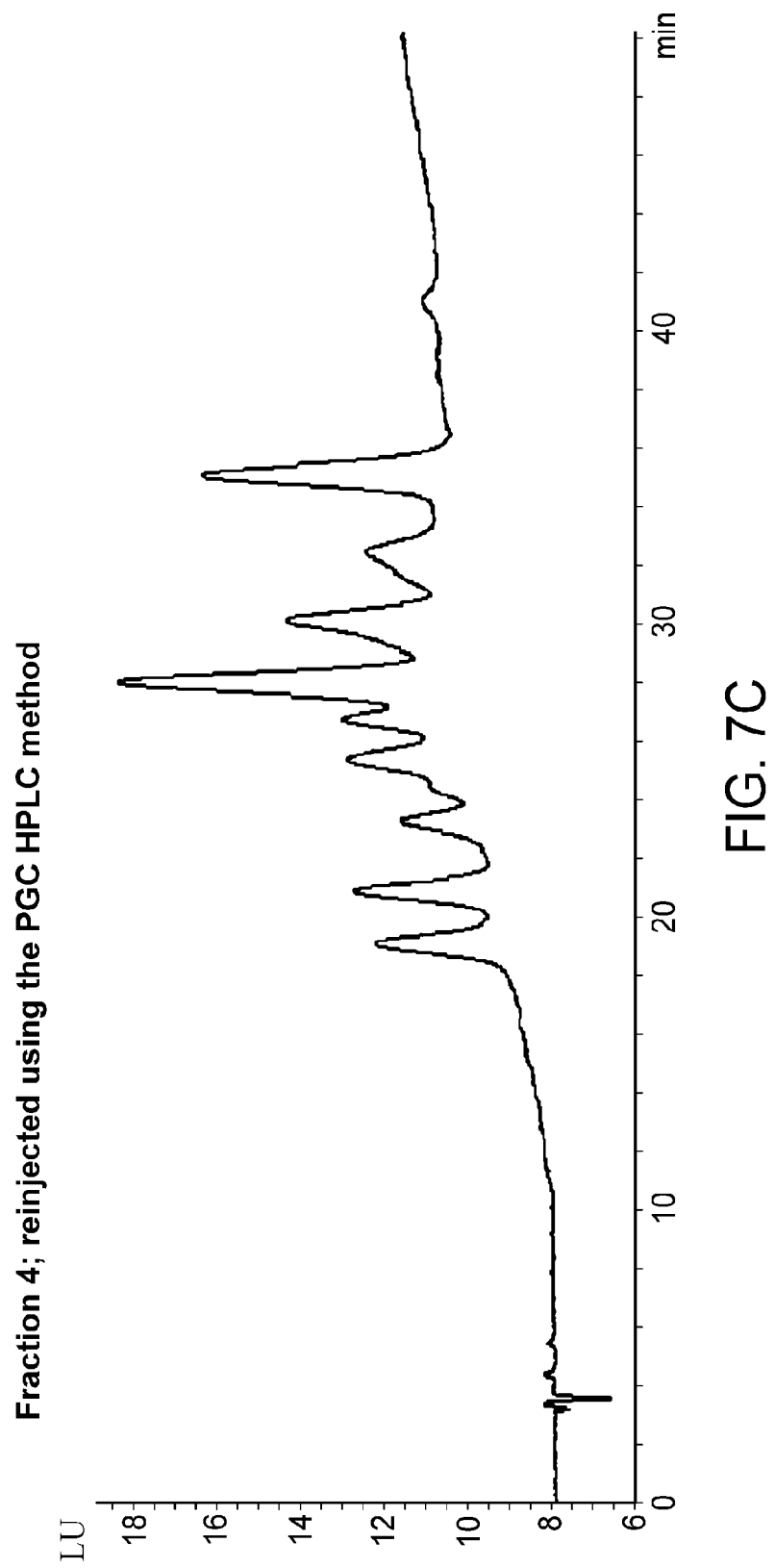

The separations in FIG. 7 were obtained using the same column and buffer system but a different set of elution gradients:

| Time (mins) | % Buffer B | | |
| --- | --- | --- | --- |
| | FIG. 7A | FIG. 7B | FIG. 7C |
| 0 | 38 | 43 | 44 |
| 5 | 38 | 43 | 44 |
| 65 | 58 | 55 | 51 |
| 66 | 80 | 80 | 80 |
| 86 | 80 | 80 | 80 |
| 87 | 38 | 43 | 44 |
| 100 | 38 | 43 | 44 |

Figure 8:
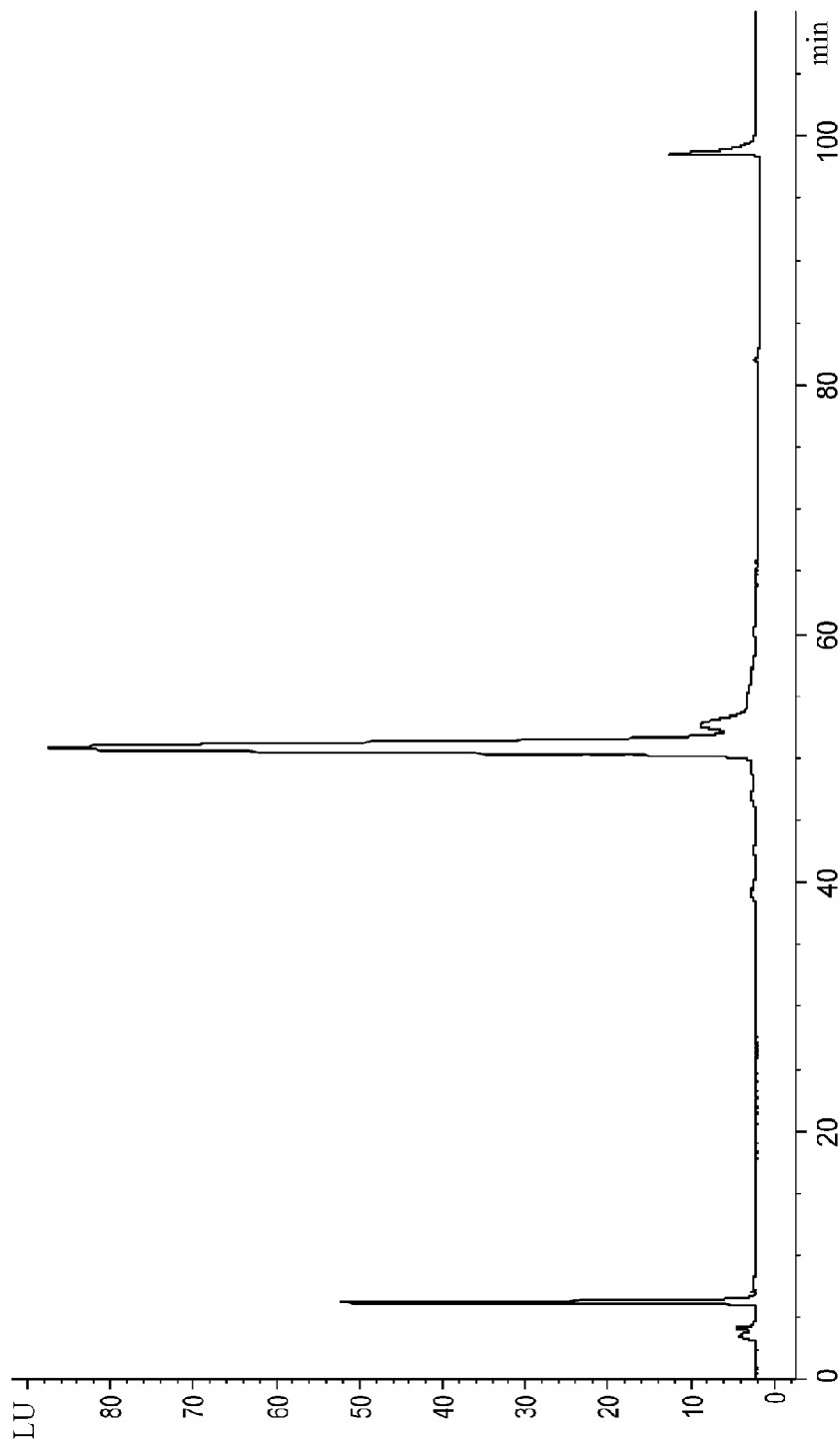
FIG. 8. Amide chromatogram for fraction 8 glycans derived via a prior AIEX (anion-exchange) chromatography.
Figure 9:
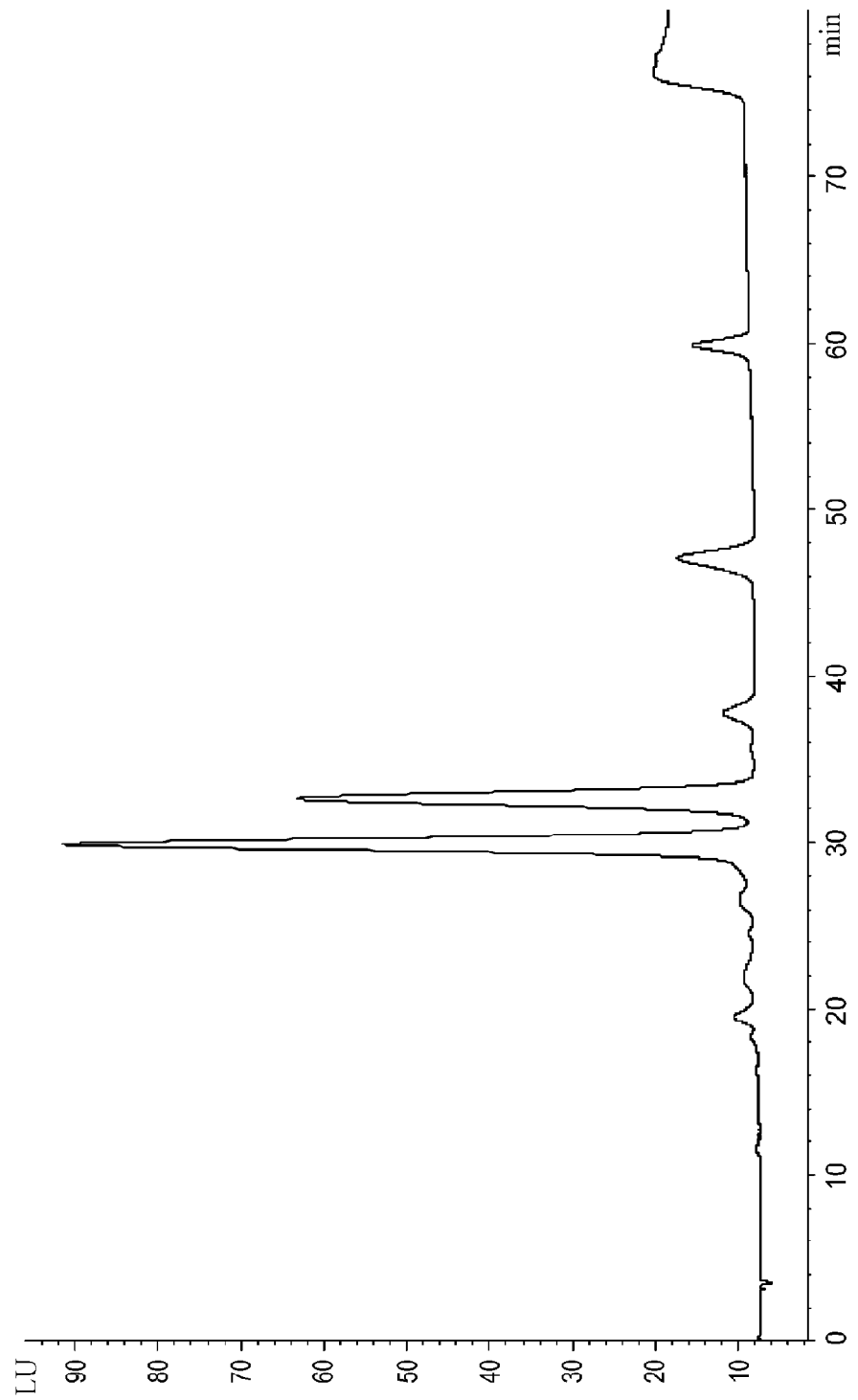
FIG. 9. PGC chromatogram for fraction 8 glycans derived via a prior AIEX (anion-exchange) chromatography. The PGC method gave surprisingly better separation than the amide method (FIG. 8) for fractions 7, 8 and 9.

FIGS. 6 and 7 show that the chromatographic resolution of fraction 4 by an amide column (FIG. 6) was comparable to that attainable by a PGC column (FIG. 7). FIGS. 8 and 9 compare the amide and PGC chromatograms for fraction 8 and show that the PGC method gave surprisingly better separation than the amide. In particular, the PGC method was able to separate glycans which were not resolvable by the amide method. Similar results were obtained for fractions 7 (see above) and 9 (data not shown).

EQUIVALENTS

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

We claim:

1. A method of monitoring production of a glycoprotein, the method comprising:
   producing a glycoprotein in a cell culture;
   removing at least a first and second sample of the glycoprotein, wherein the samples include at least one charged N-glycan;
   adding a known quantity of a reference N-glycan to the samples, wherein the reference N-glycan is labeled with a labeling agent;
   for each of the first and second samples:
      (i) separating the sample by anion-exchange chromatography to generate a plurality of fractions;
      (ii) separating a first portion of the plurality of fractions by at least one secondary chromatographic technique to obtain first separated fractions;
      (iii) separating a second portion of the plurality of fractions by at least one secondary chromatographic technique that differs from the secondary chromatographic technique from (ii) to obtain second separated fractions;
      (iv) quantifying at least one N-glycan relative to the reference N-glycan in at least a portion of the first separated fractions, or in at least a portion of the second separated fractions, or both; and
   comparing the result of (iv) from the first sample with that for the second sample.

2. The method of claim 1, wherein the at least one secondary chromatographic technique from (ii) is selected from the group consisting of reversed phase liquid chromatography (RP), normal phase liquid chromatography (NP), ion-pairing reverse phase chromatography (IP-RP), size exclusion chromatography, affinity chromatography (AC), capillary electrophoresis (CE); fluorophore-assisted carbohydrate electrophoresis (FACE); electrochromatography, and micellar electrokinetic chromatography (MEKC).

3. The method of claim 1, wherein the at least one secondary chromatographic technique from (ii) is a reversed phase chromatographic technique.

4. The method of claim 3, wherein the reversed-phase chromatographic technique employs a C18 reverse phase resin.

5. The method of claim 3, wherein the reversed-phase chromatographic technique employs a porous graphitized-carbon (PGC) resin.

6. The method of claim 1, wherein the at least one secondary chromatographic technique from (ii) is a normal phase chromatographic technique.

7. The method of claim 6, wherein the normal phase chromatographic technique employs a modified silica gel.

8. The method of claim 7, wherein the modified silica gel is selected from the group consisting of cyano-modified silica, amine-modified silica, and amide-modified silica.

9. The method of claim 1, wherein the at least one secondary chromatographic technique from (iii) is selected from the group consisting of reversed phase liquid chromatography (RP), normal phase liquid chromatography (NP), ion-pairing reverse phase chromatography (IP-RP), size exclusion chromatography, affinity chromatography (AC), capillary electrophoresis (CE); fluorophore-assisted carbohydrate electrophoresis (FACE); electrochromatography, and micellar electrokinetic chromatography (MEKC).

10. The method of claim 1, wherein the at least one secondary chromatographic technique from (iii) is a reversed phase chromatographic technique.

11. The method of claim 10, wherein the reversed-phase chromatographic technique employs a resin selected from the group consisting of a C18 reverse phase resin and a porous graphitized-carbon (PGC) resin.

12. The method of claim 1, wherein the at least one secondary chromatographic technique from (iii) is a normal phase chromatographic technique.

13. The method of claim 12, wherein the normal phase chromatographic technique employs a modified silica gel.

14. The method of claim 13, wherein the modified silica gel is selected from the group consisting of cyano-modified silica, amine-modified silica, and amide-modified silica.

15. The method of claim 1, wherein the at least one secondary chromatographic technique from (ii) is a normal phase chromatographic technique and the at least one secondary chromatographic technique from (iii) is a reverse phase chromatographic technique.

16. The method of claim 1, wherein the first portion of the plurality of fractions comprises the first half to two-thirds of the fractions from the anion exchange chromatography.

17. The method of claim 1, wherein the second portion of the plurality of fractions comprises the second half to one-third of the fractions from the anion exchange chromatography.

18. The method of claim 1, wherein the glycoprotein is a therapeutic glycoprotein.

19. The method of claim 18, wherein the therapeutic glycoprotein is an antibody.

20. The method of claim 19, wherein the antibody is a preparation of alemtuzumab, etanercept, adalimumab, abatacept, infliximab, bevacizumab, rituximab, natalizumab, or cetuximab.

* * * * *